United States Patent
Lee

(10) Patent No.: US 9,564,836 B2
(45) Date of Patent: Feb. 7, 2017

(54) TRANSDUCER, AND MANUFACTURING METHOD OF THE TRANSDUCER

(76) Inventor: Seung-Mok Lee, Izumi (JP)

(*) Notice: Subject to any disclaimer, the term of this patent is extended or adjusted under 35 U.S.C. 154(b) by 628 days.

(21) Appl. No.: 14/129,908

(22) PCT Filed: Jun. 26, 2012

(86) PCT No.: PCT/JP2012/066243
§ 371 (c)(1),
(2), (4) Date: Apr. 11, 2014

(87) PCT Pub. No.: WO2013/002207
PCT Pub. Date: Jan. 3, 2013

(65) Prior Publication Data
US 2014/0246948 A1 Sep. 4, 2014

(30) Foreign Application Priority Data

Jun. 27, 2011 (JP) .................................. 2011-141581
Jun. 27, 2011 (JP) .................................. 2011-141582

(51) Int. Cl.
*H02N 1/00* (2006.01)
*G01N 29/24* (2006.01)
(Continued)

(52) U.S. Cl.
CPC ............... *H02N 1/00* (2013.01); *B06B 1/0292* (2013.01); *B81C 1/00246* (2013.01);
(Continued)

(58) Field of Classification Search
CPC .......... B06B 1/0292; B06B 3/00; H02N 1/00; Y10T 29/49005; B81C 1/00246
(Continued)

(56) References Cited

U.S. PATENT DOCUMENTS

2008/0290756 A1* 11/2008 Huang .................. B06B 1/0292
310/300
2010/0207485 A1* 8/2010 Dirksen ................... A61B 8/00
310/300
(Continued)

FOREIGN PATENT DOCUMENTS

JP  2007-531357 A  11/2007
JP  2008-546239 A  12/2008
(Continued)

OTHER PUBLICATIONS

Arif S. Ergun, Goksen G. Yaralioglu, and Butrus T. Khuri-Yakub, "Capacitive Micromachined Ultrasonic Transducers: Theory and Technology", Journal of Aerospace Engineering (c) ASCE, Apr. 2003, p. 76-84.

*Primary Examiner* — Thanh Lam
(74) *Attorney, Agent, or Firm* — Masuvalley & Partners

(57) ABSTRACT

A transducer, and a method for manufacturing the transducer are provided. The transducer includes a substrate-side electrode provided in one side of an insulative substrate and an opposite plate including an opposite electrode disposed opposite to the substrate-side electrode, and which performs a function such as a reduction in impedance, conversion of capacitance, signal amplification, thereby achieving size reduction of the transducer itself. An upper plate is made of a silicon monocrystal and is arranged so as to face a substrate-side electrode. In the upper plate, an integrated circuit section which is an impurity region of an IC circuit is formed by a thermal diffusion method or an ion implantation method. By this transducer, an improvement in conversion efficiency, an improvement in productivity, and a size reduction of a mount system are achieved.

16 Claims, 18 Drawing Sheets

(51) Int. Cl.
*B06B 1/02* (2006.01)
*B81C 1/00* (2006.01)
*G01H 11/06* (2006.01)
*H01L 29/84* (2006.01)

(52) U.S. Cl.
CPC ......... *G01H 11/06* (2013.01); *G01N 29/2406* (2013.01); *B81B 2201/0271* (2013.01); *B81B 2207/015* (2013.01); *B81C 2203/031* (2013.01); *B81C 2203/075* (2013.01); *H01L 29/84* (2013.01)

(58) Field of Classification Search
USPC .............................. 310/300; 438/53; 29/594
See application file for complete search history.

(56) References Cited

U.S. PATENT DOCUMENTS

| | | | | |
|---|---|---|---|---|
| 2010/0225200 | A1* | 9/2010 | Kupnik | B06B 1/0292 310/300 |
| 2012/0068571 | A1* | 3/2012 | Chen | B06B 1/0292 310/300 |
| 2012/0256518 | A1* | 10/2012 | Torashima | B06B 1/0292 310/300 |
| 2013/0257218 | A1* | 10/2013 | Dehe | H04R 7/10 310/300 |

FOREIGN PATENT DOCUMENTS

| | | |
|---|---|---|
| JP | 2011-507561 A | 3/2011 |
| JP | 2011-101163 A | 5/2011 |

\* cited by examiner

TRANSDUCER, AND MANUFACTURING METHOD OF THE TRANSDUCER

This application is a national phase application under 35 U.S.C. §371 of International Application Serial No. PCT/JP2012/066243, filed on Jun. 26, 2012, and claims priority under 35 U.S.C. §119 to Japanese Patent Application No. 2011-141581, filed on Jun. 27, 2011, and Japanese Patent Application No. 2011-141582, filed on Jun. 27, 2011 which are hereby expressly incorporated herein by reference in their entirety for all purposes.

FIELD OF THE INVENTION

The present invention relates to a transducer comprising a substrate-side electrode provided in one side of an insulative substrate and an opposite plate provided with an opposite electrode disposed opposite to the substrate-side electrode, and to a manufacturing method of the transducer.

BACKGROUND OF THE INVENTION

FIG. 1 is a sectional view schematically showing an example of a configuration of the conventional CMUT (Capacitive Micromachined Ultrasonic Transducer)-type ultrasonic transducer.

The conventional CMUT-type ultrasonic transducer comprises a substrate 104, a vibrating membrane 105 which sends and receives an ultrasonic wave, and a vibrating-membrane supporting section 101 which is provided in one side of the substrate 104 and supports the vibrating membrane 105 so that the vibrating membrane 105 faces the substrate 104. Also, a membrane-side electrode 102 formed in the vibrating membrane 105 is disposed opposite to a substrate-side electrode 103 formed in the substrate 104.

In the CMUT-type ultrasonic transducer provided with the above-described configuration, when the vibrating membrane 105 receives an ultrasonic wave (sound pressure), the vibrating membrane 105 and the membrane-side electrode 102 vibrate, and the ultrasonic transducer sends an electric signal concerning the received ultrasonic wave, based on the capacitance change which occurs at the time of vibration between the membrane-side electrode 102 and the substrate-side electrode 103. Also, DC voltage and AC voltage are applied between the membrane-side electrode 102 and the substrate-side electrode 103, thereby the vibrating membrane 105 vibrates and the vibrating membrane 105 sends an ultrasonic wave. Such a CMUT-type ultrasonic transducer has an excellent frequency response such as a wide band, a high sensitivity.

For example, the non-patent literature 1 discloses such a conventional CMUT-type ultrasonic transducer and a manufacturing method thereof. In the CMUT-type ultrasonic transducer described in the non-patent literature 1, at the time of a later-described wet etching, a nitride layer for protecting a substrate is formed on a silicon substrate, and a so-called sacrifice layer containing polycristal silicon is vapor-deposited on the nitride layer. Then, both a vibrating membrane containing nitride and a vibrating-membrane supporting section are vapor-deposited on the sacrifice layer, and a hole for removing the sacrifice layer is formed in the vibrating membrane, and then the sacrifice layer is removed by wet etching. Subsequently, the hole is filled, a membrane-side electrode is vapor-deposited on the vibrating membrane, and then a protective layer is formed on the membrane-side electrode.

PRIOR ART LITERATURE

Non-Patent Literature

Non-patent literature 1: [Capacitive Micromachined Ultrasonic Transducers: Theory and Technology], JOURNAL OF AEROSPACE ENGINEERING, USA, April, VOL. 16, NO. 2, p. 76-84

SUMMARY OF THE INVENTION

Problem(s) to be Solved by the Invention

On the other hand, various problems occur in the above-described conventional ultrasonic transducer during the actual use. In detail, there is a problem in which, when the ultrasonic transducer is used at a high frequency, an impedance increases, thereby an actual drive voltage to be applied to the electrode lowers as compared with an input voltage. Moreover, in a case where the number of transducers is small in an array provided with a plurality of ultrasonic transducers, there is a problem in which an impedance increases due to a small base capacitance in the array and a so-called S/N ratio lowers, and the like.

Since a signal sent from a device provided with the above-described ultrasonic transducer or array appears as a capacitance change, a converter circuit for converting the signal to a voltage signal and an amplifier circuit for the signal, and a circuit for the impedance adjust etc. are required. Although it is not necessary to provide a circuit on an 1D array CMUT device especially, it is necessary to provide a circuit on a CMUT device for high frequency or 2D array, or on a periphery thereof in order to improve an impedance matching or S/N ratio. However, it is difficult to ensure a space where the peripheral circuits are efficiently provided for the microminitualization of the device, and since a process for mounting them is complicated even if there is a space, the productivity of the whole system lowers.

In a case where an integrated circuit is required for the existing CMUT device structure, a through electrode is provided on a silicon substrate and the integrated circuit is provided on back side of the device. However, a process for forming a through electrode for such a structure is complicated, the productivity is low, and a parasitic capacitance may arise from a through electrode Moreover, in a case where a silicon monocrystal is used as a substrate, there is a problem in which a so-called parasitic capacitance arises due to a conductivity of the silicon monocrystal therefore the conversion efficiency of the device lowers. However, such a problem cannot be dissolved in the ultrasonic transducer described in the above non-patent literature 1.

The present invention has been made with the aim of solving the above problems, and it is an object of the invention to provide a transducer comprising a substrate-side electrode provided on one side of an insulative substrate, and an opposite plate including an opposite electrode disposed opposite to the substrate-side electrode, thereby improving the impedance increase and achieving the size reduction of the transducer itself, a device provided with the transducer and a mount system provided with the device, and to provide a manufacturing method for manufacturing the transducer.

Means for Solving the Problem

The First Invention

The transducer according to the present invention is a transducer comprising a substrate-side electrode provided in one side of an insulative substrate and an opposite plate including an opposite electrode disposed opposite to the substrate-side electrode, the transducer generating a signal based on a change of a gap between the substrate-side electrode and the opposite electrode, wherein the opposite plate is made of silicon monocrystal, and is provided with an integrated circuit section for performing a processing concerning the signal.

The transducer according to the present invention is characterized in that the integrated circuit section is an impurity region, and is electrically connected to the opposite electrode.

The transducer according to the present invention is characterized by further comprising a holding section which is provided in the substrate so as to project and holds the opposite plate, wherein the integrated circuit section is provided at a position which matches the holding section.

The transducer according to the present invention is characterized in that the opposite plate is provided in one side of the opposite plate facing the substrate and at a position where the opposite plate contacts the holding section.

The method for manufacturing a transducer according to the present invention is a method for manufacturing a transducer comprising a substrate-side electrode provided in one side of an insulative substrate and an opposite plate including an opposite electrode disposed opposite to the substrate-side electrode, the transducer generating a signal based on a change of a gap between the substrate-side electrode and the opposite electrode, comprising an integrated-circuit-section forming process of forming an integrated circuit section for performing a processing concerning the signal in an opposite plate made of silicon monocrystal.

The method for manufacturing a transducer according to the present invention is characterized in that the integrated circuit section is an impurity region, and is electrically connected to the opposite electrode.

The method for manufacturing a transducer according to the present invention is characterized in that in the integrated-circuit-section forming process, the opposite electrode is formed.

In the present invention, the opposite plate made of silicon monocrystal is arranged so as to face the substrate-side electrode, and the integrated circuit section is provided in the opposite plate to perform a signal processing necessary to the transducer. For example, the integrated circuit section lowers an impedance and performs a function such as the conversion of capacitance, signal amplifier.

In the present invention, the integrated circuit section is an impurity region of an IC circuit, which is formed by the thermal diffusion method or ion implantation method, for example. The integrated circuit section is electrically connected to the opposite electrode and performs a signal processing necessary to the device. For example, the integrated circuit section lowers an impedance, and performs a function such as the conversion of capacitance, signal amplifier.

In the present invention, the integrated circuit section is provided at a position of the opposite plate matching the holding section for holding the opposite plate.

In the present invention, the integrated circuit section can be provided at a position where the opposite plate contacts the holding section for holding the opposite plate.

The Second Invention

The transducer according to the present invention is A transducer comprising a substrate-side electrode provided in one side of an insulative substrate and an opposite plate including in one side an opposite electrode disposed opposite to the substrate-side electrode, the transducer generating a signal based on a change of a gap between the substrate-side electrode and the opposite electrode, further comprising: a holding section which is provided in one side of the opposite plate so as to project and holds the opposite plate; and an integrated circuit section which is provided in the holding section and performs a processing concerning the signal.

The transducer according to the present invention is characterized in that the integrated circuit section is an impurity region, and is electrically connected to the opposite electrode.

The transducer according to the present invention is characterized in that the holding section is provided with the integrated circuit sections at a plurality of places.

The transducer according to the present invention is characterized in that the holding section includes a multilayer structure, and the integrated circuit sections are provided in a plurality of layers.

The transducer according to the present invention is characterized in that a groove section is provided in the one side of the substrate, and an end part of the holding section on a side of the substrate is inserted into the groove section.

The transducer according to the present invention is characterized in that the groove section is configured so that sizes in an opposite direction of the substrate-side electrode and the opposite electrode are sizes according to a size of the holding section in the opposite direction.

The method for manufacturing a transducer according to the present invention is a method for manufacturing a transducer comprising a substrate-side electrode provided in one side of an insulative substrate and an opposite plate including in one side an opposite electrode disposed opposite to the substrate-side electrode, the transducer generating a signal based on a change of a gap between the substrate-side electrode and the opposite electrode, comprising an integrated-circuit-section forming process of forming an integrated circuit section for performing a processing concerning the signal in a holding section which is provided in one side of the opposite plate so as to project and holds the opposite plate.

The method for manufacturing a transducer according to the present invention is characterized in that the integrated circuit section is an impurity region, and is electrically connected to the opposite electrode.

The method for manufacturing a transducer according to the present invention is characterized in that the holding section is formed by a lamination process, and during the lamination process the integrated-circuit-section forming process is performed.

In the present invention, the holding section is provided in the one side of the opposite plate so as to project, and the integrated circuit section is provided in the holding section to perform a signal processing necessary to the transducer. For example, the integrated circuit section lowers an impedance, and performs a function such as the conversion of capacitance, signal amplifier.

In the present invention, the integrated circuit section is an impurity region of an IC circuit, which is formed by the thermal diffusion method or ion implantation method, for example, and is electrically connected to the opposite electrode to perform a signal processing necessary to the device. For example, the integrated circuit section lowers an impedance and performs a function such as the conversion of capacitance, signal amplifier.

In the present invention, the integrated circuit sections are provided at a plurality of places of the holding section.

In the present invention, the holding section has a multilayer structure made of a plurality of layers, and the integrated circuit section is provided for each layer or in the plurality of layers.

In the present invention, the end part of the holding section in the opposite direction of the substrate and opposite plate is inserted into the groove section. That is, the gap between the substrate and opposite plate is small by a sized of the groove section in the opposite direction.

In the present invention, the size of the groove section in the opposite direction of the substrate-side electrode and opposite electrode is determined in advance according to the size of the holding section in the opposite direction. That is, in a case where the size of the holding section in the opposite direction is larger than the gap between the substrate-side electrode and opposite electrode, the size of the groove section is determined so as to keep the gap constant.

Effect of the Invention

According to the first and second inventions, it is possible to achieve the improvement in impedance rise, the conversion of capacitance, the signal amplifier and the like by the integrated circuit section and the electrical characteristics in the transducer can be enhanced.

Since the integrated circuit section of the first present invention is an impurity region formed in the opposite plate, it is not necessary to mount another element for the effect, thereby achieving the size reduction of the transducer itself, the device provided with the transducer and the mount system comprising the device and the improvement in productivity. Also, according to the present invention, since the other peripheral circuit such as the opposite electrode is formed when the integrated circuit section is formed, the manufacturing process shortens and the manufacturing cost is reduced.

Furthermore, since the integrated circuit section is an impurity region formed in the holding section, it is not necessary to mount another element for the effect, thereby achieving the size reduction of the transducer itself, the device provided with the transducer and the mount system comprising the device and the improvement in productivity.

In addition, according to the second present invention, the integrated circuit section is formed during the process of forming the holding section having the multilayer structure. Therefore, it is possible to form the integrated circuit section for each layer or in a plurality of layers and to efficiently form a plurality of integrated circuit sections in a limited space of the holding section when the integrated circuit section is formed.

BRIEF DESCRIPTION OF THE DRAWINGS

FIG. 1 is a sectional view schematically showing an example of a configuration of the conventional CMUT-type ultrasonic transducer.

FIG. 2 is a longitudinal sectional view showing a configuration of a main part of a transducer array according to Embodiment 1 of the second present invention.

FIG. 3 is a partial schematic view showing the transducer array according to Embodiment 1 of the second present invention seen from above without showing a part thereof.

FIG. 4 is a schematic sectional view for explaining a configuration of the transducer according to Embodiment 1 of the second present invention.

FIG. 5 is an explanation view for explaining a method for manufacturing the transducer and transducer array according to Embodiment 1 of the second present invention.

FIG. 6 is an explanation view for explaining a method for manufacturing the transducer and transducer array according to Embodiment 1 of the second present invention.

FIG. 7 is a schematic sectional view for explaining a configuration of the transducer according to Embodiment 2 of the second present invention.

FIG. 8 is a schematic sectional view for explaining a configuration of a transducer according to Embodiment 3 of the second present invention.

THE CONFIGURATION FOR INVENTING

<The Mode for Implementing the First Present Invention>

The following description will explain a transducer and a method for manufacturing the transducer according to the present invention, based on the drawings specifically. The description is made based on the example of a transducer array provided with a plurality of the transducers.

Embodiment 1

Figure 1:
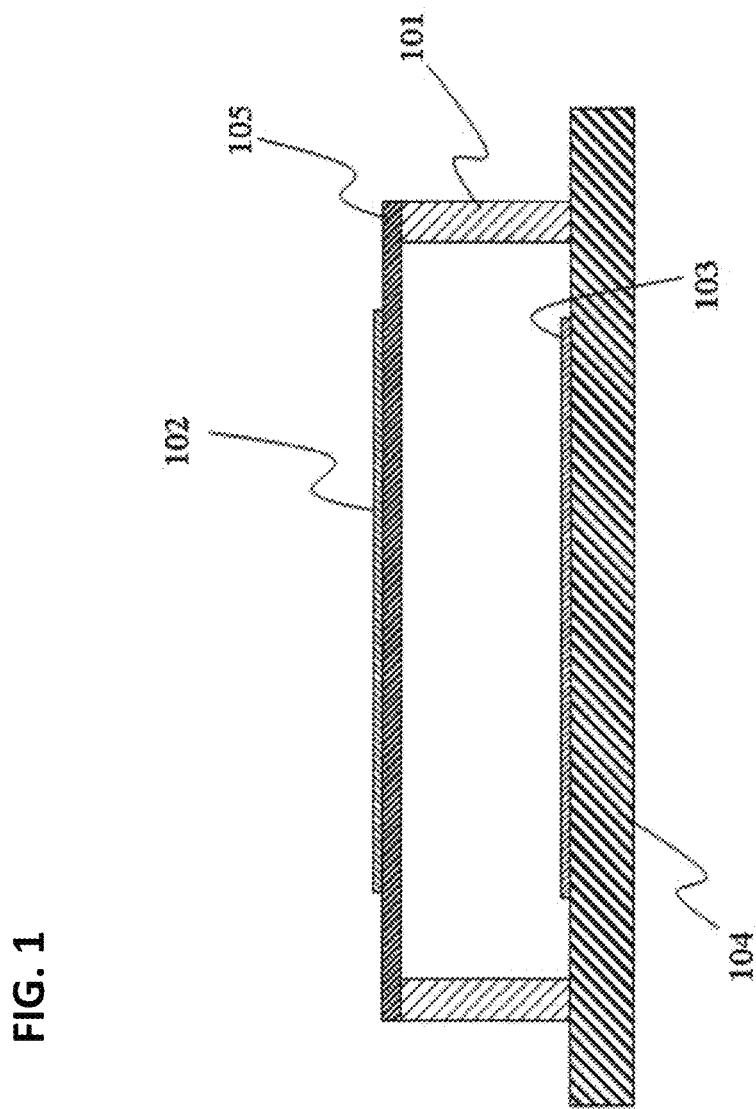
FIG. 1 is a sectional view showing an example of a configuration of the conventional CMUT-type ultrasonic transducer.
Figure 2:
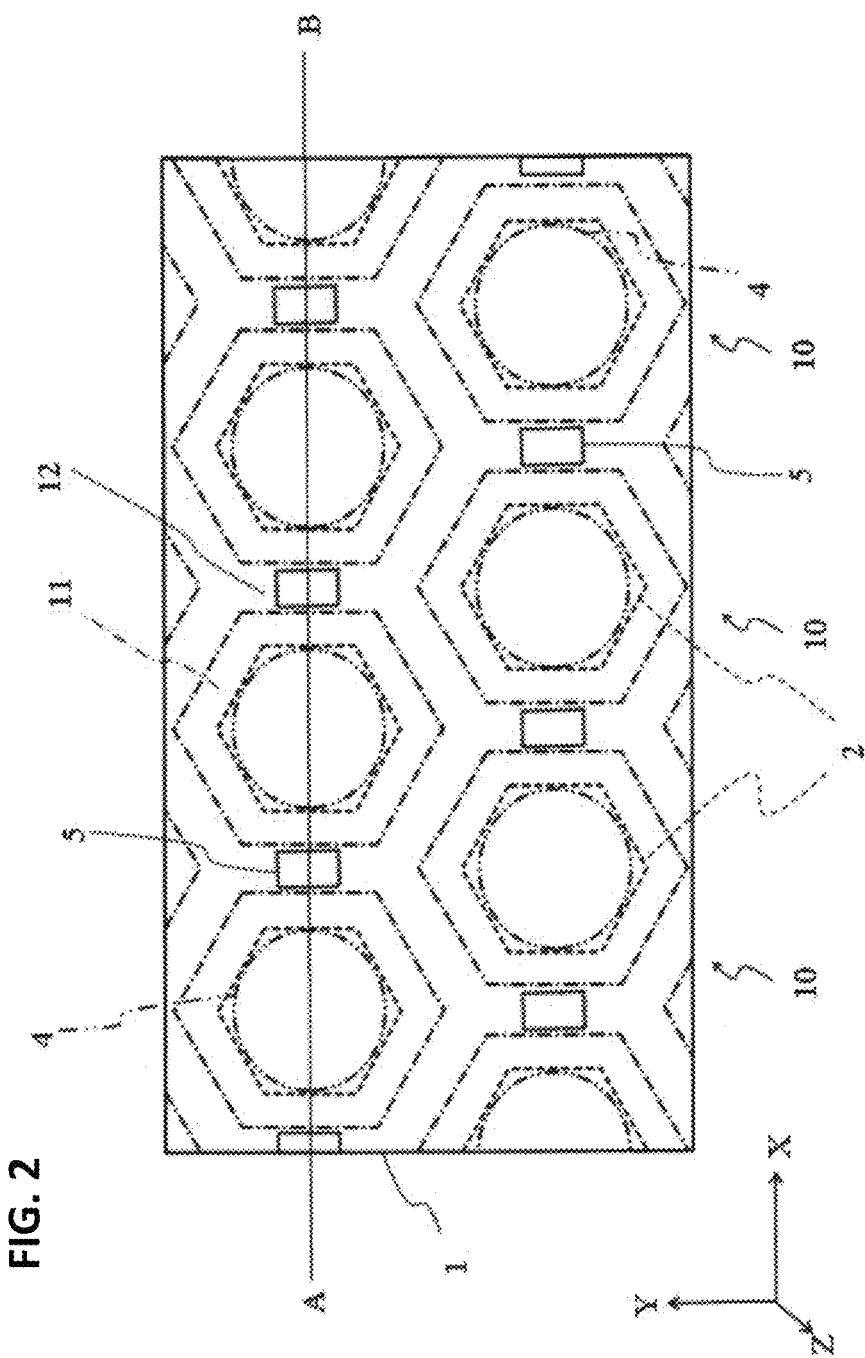
FIG. 2 is a partial schematic view showing a transducer array according to Embodiment 1 of the first present invention seen in the Z axial direction.
Figure 3:
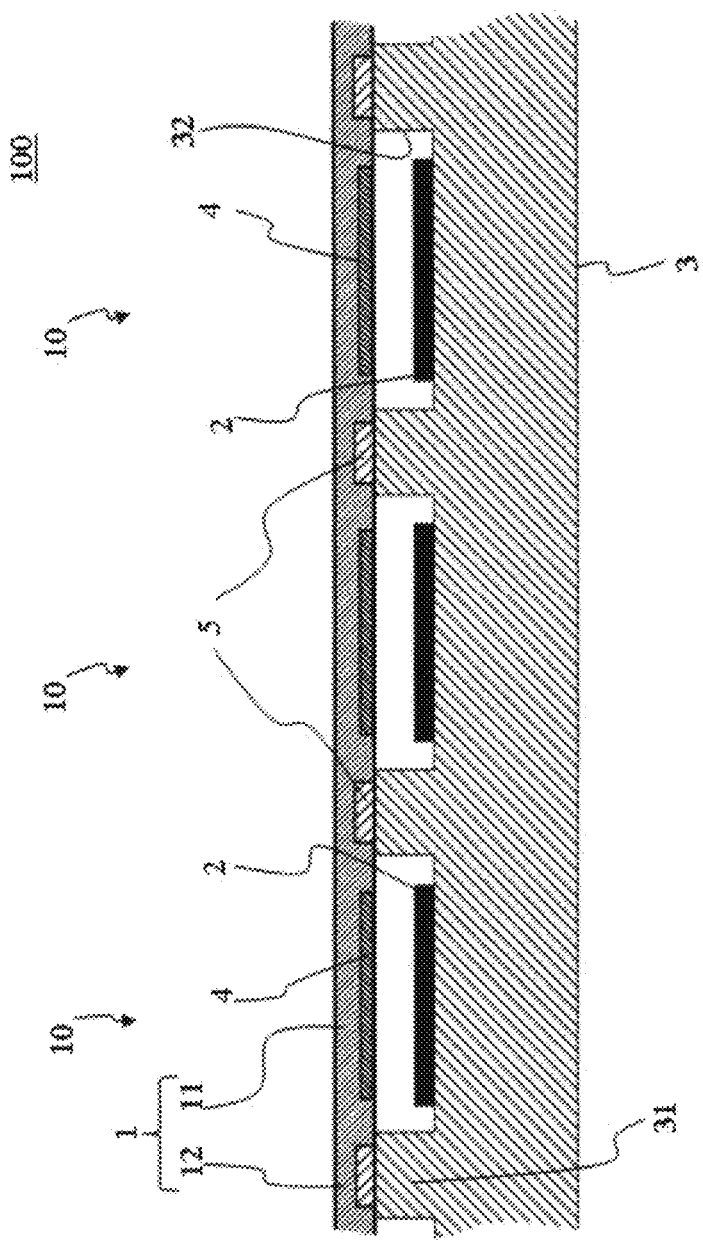
FIG. 3 is a sectional view taken along the A-B line of FIG. 2.

FIG. 2 is a partial schematic view showing a transducer array according to Embodiment 1 of the present invention seen in the Z axial direction, and FIG. 3 is a sectional view taken along the A-B line of FIG. 2. In the drawings, the reference number 10 designates the transducer according to the present invention, and the reference number 100 designates the transducer array provided with a plurality of transducers 10. For convenience of explanation, the Z axial direction is explained as a vertical direction in the following description.

The transducer array 100 is provided with a plurality of transducers 10 disposed on one substrate 3 in the X axial direction and Y axial direction. The transducer array 100 converts an ultrasonic wave received by each transducer 10 to an electric signal, and sends it to an external device. The external device generates image data based on the electric signal sent from the transducer array 100 (transducer 10).

Figure 4:
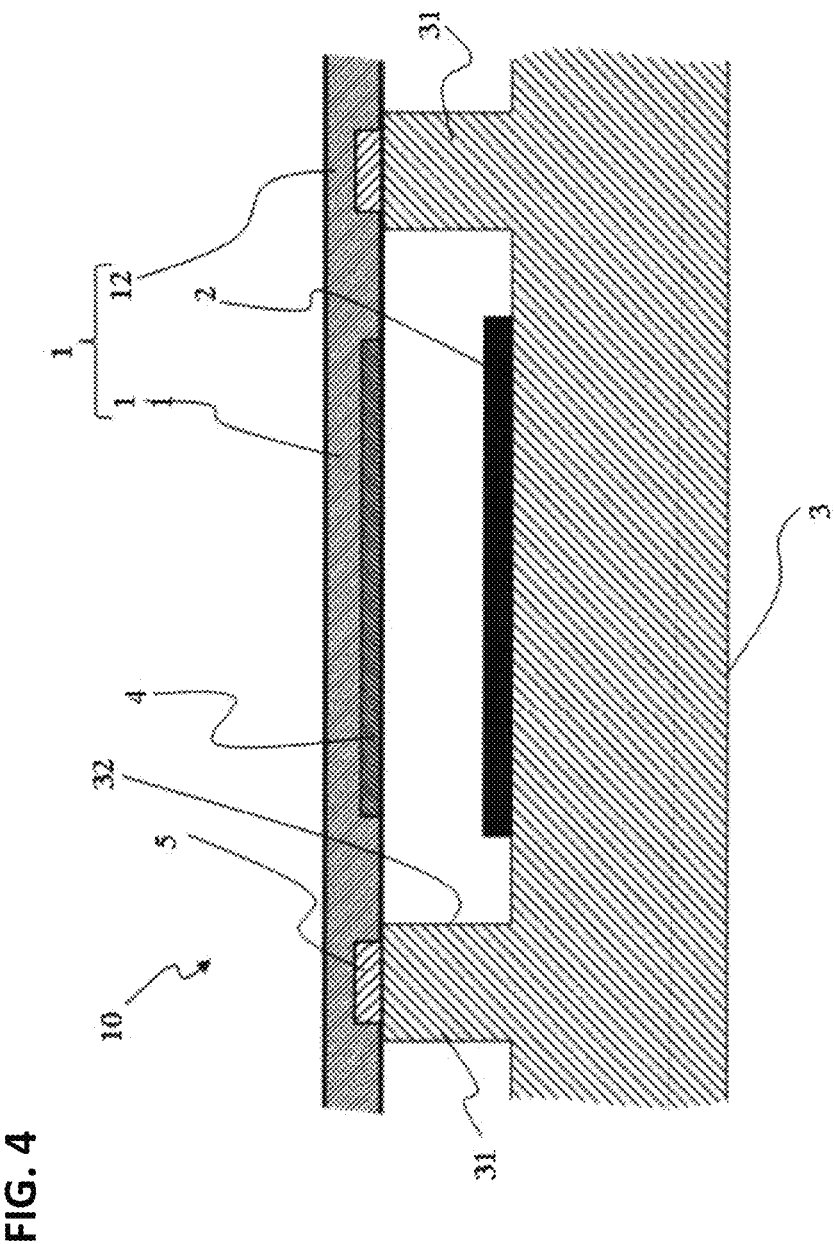
FIG. 4 is a schematic sectional view for explaining the configuration of the transducer according to Embodiment 1 of the first present invention.

FIG. 4 is a schematic sectional view for explaining the configuration of the transducer 10 according to Embodiment 1 of the present invention.

The transducer 10 of the transducer array 100 according to Embodiment 1 of the present invention comprises a substrate 3 and an upper plate 1 arranged above the substrates 3 so as to face the substrate 3. A recess portion 32 is provided in a top face of the substrate 3 facing a bottom face of the upper plate 1, and a substrate-side electrode 2 is provided on a bottom of the recess portion 32.

The upper plate 1 includes a vibrating membrane section 11 which vibrates upon sending or receiving an ultrasonic wave, and a contact section 12 which matches to a position of a later-described holding section 31 in the Z axial direction and contacts the holding section 31. A bottom face of the contact section 12 is bonded to an upper end part of the holding section 31, and the upper plate 1 is fixed to the substrate 3.

The vibrating membrane section 11 is a part of the upper plate 1 corresponding to a position which faces the substrate-side electrode 2. The adjacent vibrating membrane sections 11 with the contact section 12 therebetween are formed at a distance. That is, a periphery of the vibrating membrane section 11 is surrounded by the contact section 12, and the contact section 12 is bonded to the holding section 31 thereby enabling the vibration of the vibrating membrane section 11.

For example, the substrate 3 is made of glass such as Pyrex glass (registered trademark), quartz, Tempax (registered trademark), Foturanglass (registered trademark), and has a thickness of 500 μm or more. As described above, the recess portion 32 is formed in the top face of the substrate 3, and the substrate-side electrode 2 is vapor-deposited in a central portion of a bottom of the recess portion 32.

Note that, the thickness of the substrate 3 is not limited to the above description, and includes the range of 1 μm to 10 cm. For example, the thickness may be 300 μm or more and 500 μm or less.

The recess portion 32 is provided in the top face of substrate 3 so as to be a hexagon in a plan view. A land is formed between the recess portions 32 of the transducer 10, the land being formed by a residual portion by the provision of the recess portion 32. The land functions as the holding section 31 which holds the upper plate 1. That is, the upper plate 1 (contact section 12) is bonded to an upper end face of the holding section 31, thereby it is held by the substrate 3.

The substrate-side electrode 2 is hexagonal plate-shaped, similarly to the recess portion 32, and has an area of 700 $\mu m^2$ or less, for example. Also, the substrate-side electrode 2 has the thickness of 0.1 to 1.0 μm, for example, and is made of Ni, Cr, Al, Pt, Au, etc.

Moreover, an insulation membrane (not shown) is vapor-deposited in the top face of the substrate-side electrode 2, and the insulation membrane is made of oxide, for example and insulates the upper plate 1 (vibrating membrane section 11) from the substrate-side electrode 2.

The inside of the recess portion 32 is hexagonal cylinder-shaped in a transversal view, for example. A size of one side of the hexagon is 22 μm and a distance between opposite sides thereof is 38 μm. A shape of the recess portion 32 is not limited to be hexagonal cylinder-shaped, but may be circular cylinder-shaped.

A size in the vertical direction of the holding section 31, in other words, a gap between the bottom face of the upper plate 1 and the top face of the substrate 3 is 0.05 to 10 μm, for example. It is more preferred that it is 0.1 to 3 μm. Also, the holding section 31 has a size in the lateral direction, that is, a wall thickness of 8 to 16 μm, for example. Note that the contact section 12 of upper plate 1 is bonded to the top face of holding section 31, in other words, the top face of substrate 3 by a so-called anodic bonding method.

The anodic bonding method is generally a method for closely bonding glass to silicon or metal at the temperature of about 400 degrees or less. It is a method for overlapping glass with silicon or metal and applying heat and voltage, thereby cation in glass is forcedly diffused to silicon or metal and an electrostatic attraction occurs between glass, silicon, metal etc. and chemical bonding is performed therein. Therefore, it is a method that allows favorable bonding even at a relatively low temperature.

Accordingly, the transducer 10 according to Embodiment 1 of the present invention controls stress concentration due to the deformation which tends to occur in the process of bonding at a high temperature, and the stress concentration occurring in a bond portion between the holding section 31 and the upper plate 1. Furthermore, it controls the lowering of the conversion efficiency or sensitivity due to the stress's influence on the vibrating membrane section 11, and has an excellent structural reproducibility in manufacturing.

The case in which the wall thickness of the holding section 31 is 8 to 16 μm is explained as an example, but it is not limited to this. For example, the wall thickness may be 1 to 16 μm.

The upper plate 1 faces the substrate 3 and is provided so as to cover the recess portion 32. Therefore, an inner peripheral face of the recess portion 32 and the bottom face of the upper plate 1 form a space.

The thickness of the upper plate 1 is 1.5 μm, for example, but it is not limited to this and may be 0.5 to 3 μm. The upper plate 1 is made of silicon monocrystal whose resistance value is 10000 Ωcm or more. Therefore, in the transducer 10 and transducer array 100 according to Embodiment 1 of the present invention, an electric charge is pooled in the vibrating membrane section 11 in applying voltage, so the charge phenomenon is preventer from occurring when the vibrating membrane section 11 is operated upon the application of AC voltage of a few to several tens of MHz.

In the bottom face of the vibrating membrane section 11, an opposite electrode 4 corresponding to the substrate-side electrode 2 is formed. The opposite electrode 4 is an impurity region formed directly above the substrate-side electrode 2. The opposite electrode 4 is formed in a range of circle in a plan view, and is a so-called conductive impurity region obtained by subjecting an N-type or P-type chemical element to a thermal diffusion method or an ion implantation method.

For example, an integrated circuit section 5 is formed on the bottom face of the contact section 12. The integrated circuit section 5 is an impurity region formed at a position facing the top face of the holding section 31. In detail, the integrated circuit section 5 is an IC circuit obtained by subjecting a chemical element such as 5 group (N-type) of As, P, Sb etc. or 3 group (P-type) of Al, B, Ga etc. to the thermal diffusion method or ion implantation method at such a position of the upper plate 1.

Note that the position at which the integrated circuit section 5 is formed is not limited to the bottom face of the contact section 12. It may be any position of the upper plate 1 except for a region concerning the opposite electrode 4.

The integrated circuit section 5 is formed to function as a variable-capacitance capacitor, a resistance, a capacitor etc. which lowers an impedance. The integrated circuit section 5 is electrically connected to the opposite electrode 4, lowers an impedance occurring in the transducer 10 or transducer array 100 and has the function such as the conversion of capacitance, signal amplification and the like.

The transducer 10 according to Embodiment 1 of the present invention comprises the integrated circuit section 5 as described above, therefore, it can avoid the problem of impedance increase at a high frequency, the problem in which an impedance increases in a case where the number of the transducer is low, and the problem in which a so-called parasitic capacitance occurs so an efficient lowers in a case where silicon monocrystal is used as the vibrating membrane, before something happens.

Moreover, in the transducer 10 according to Embodiment 1 of the present invention, the integrated circuit section 5 is formed in the contact section 12 to form an impurity region, as described above, thereby it does not require to additionally mount a peripheral circuit for the reduction in impedance and signal processing, does not exert an influence on the vibration of the vibrating membrane section 11, and achieves the size reduction of the transducer itself and device.

Moreover, the transducer 10 according to Embodiment 1 of the present invention comprises the opposite electrode 4 and integrated circuit section 5 formed in the bottom face of the upper plate 1, so it does not require a protective membrane for protecting the opposite electrode 4 and integrated circuit section 5.

Note that the transducer 10 according to Embodiment 1 of the present invention comprises the opposite electrode 4 formed in the upper plate 1 as the impurity region and a part of the upper plate 1 (vibrating membrane section 11) also functions as the so-called vibrating membrane thereby achieving the size reduction of the device further.

The transducer array 100 according to Embodiment 1 of the present invention applies voltage between the substrate-side electrode 2 and the opposite electrode 4 of the upper plate 1 corresponding to the substrate-side electrode 2 in each of the plurality of transducers 10, thereby vibrating the vibrating membrane section 11 to send an ultrasonic wave to the outside, and obtaining an electric signal concerning a change of a capacitance between the substrate-side electrode 2 and the opposite electrode 4 due to the vibration of the vibrating membrane section 11 based on the ultrasonic wave reflected from the outside to obtain a so-called ultrasonic image based on the electric signal.

Figure 5:
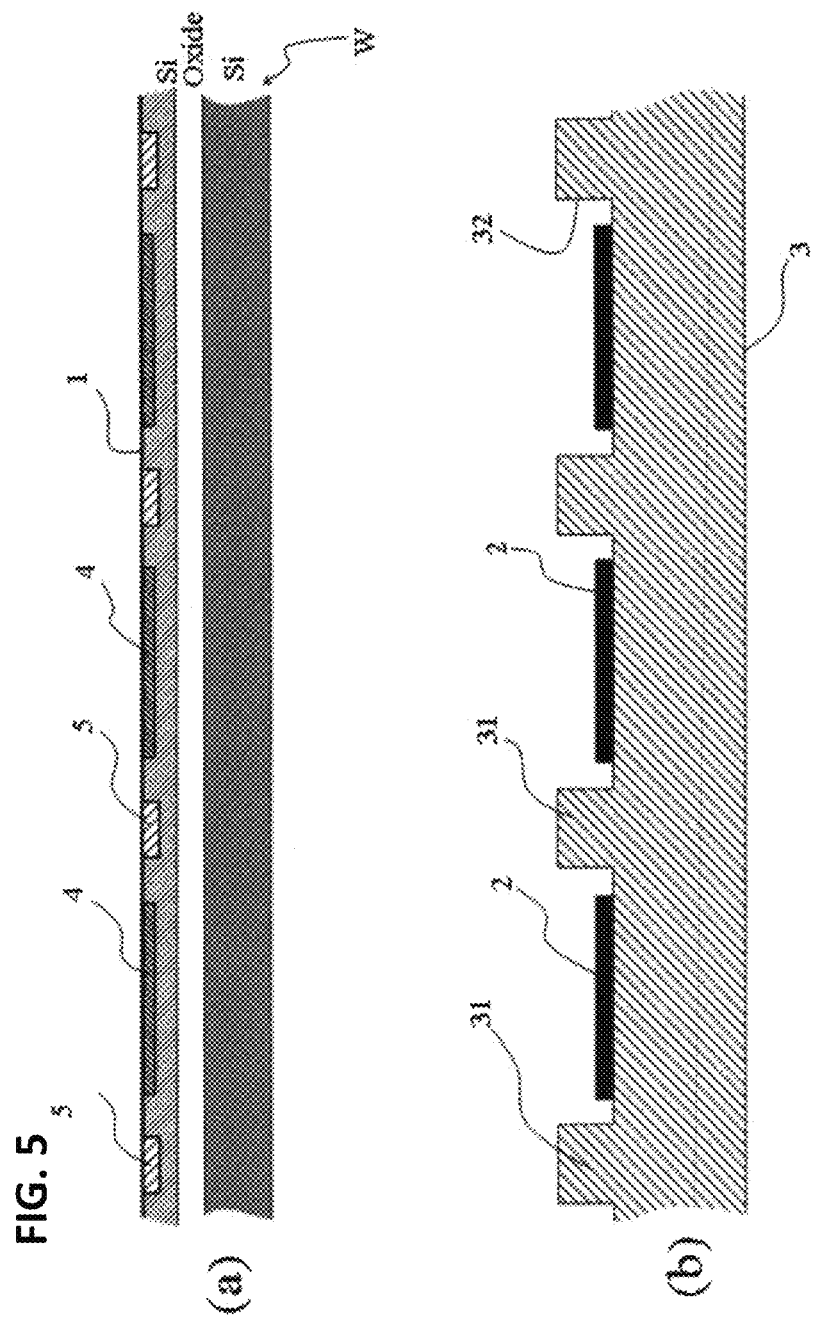
FIG. 5 is an explanation view for explaining a method for manufacturing the transducer and a transducer array according to Embodiment 1 of the first present invention.
Figure 6:
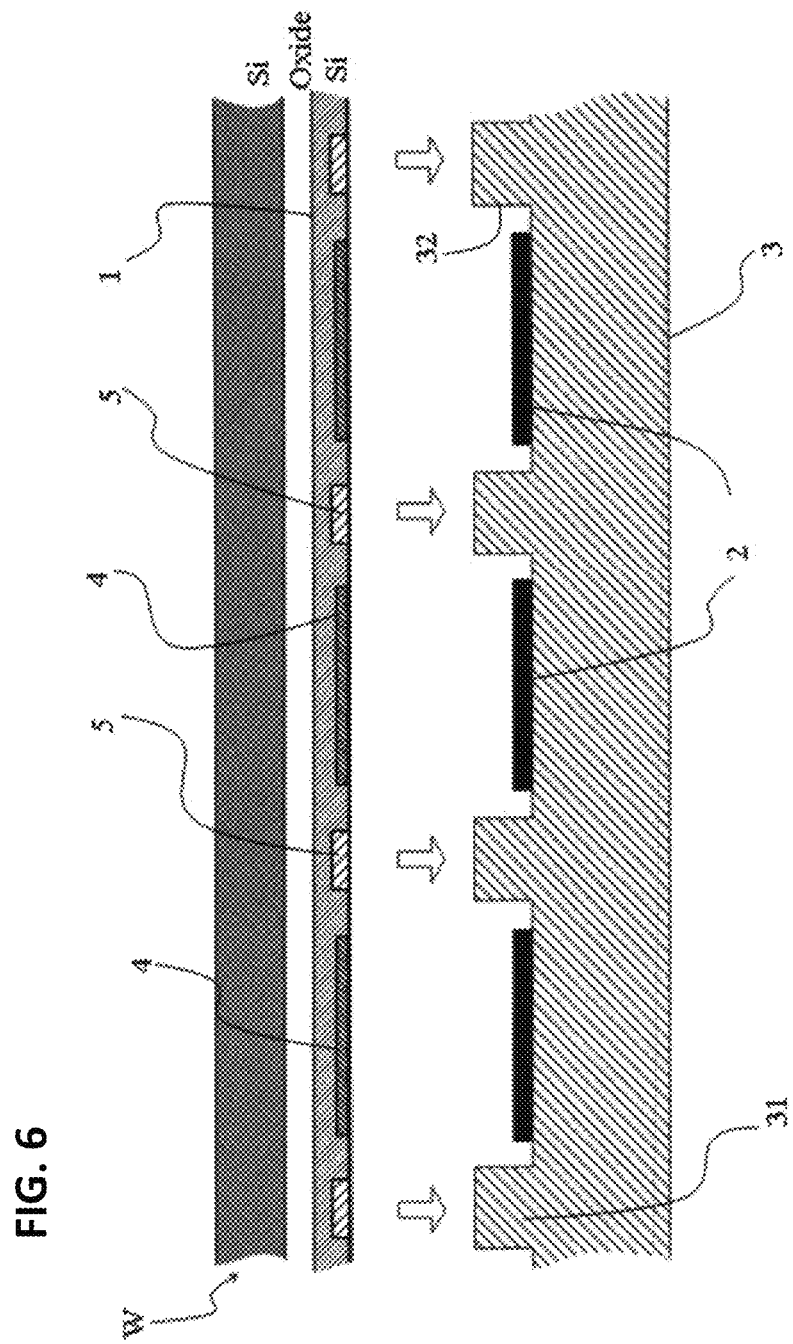
FIG. 6 is an explanation view for explaining a method for manufacturing the transducer and transducer array according to Embodiment 1 of the first present invention.
Figure 7:
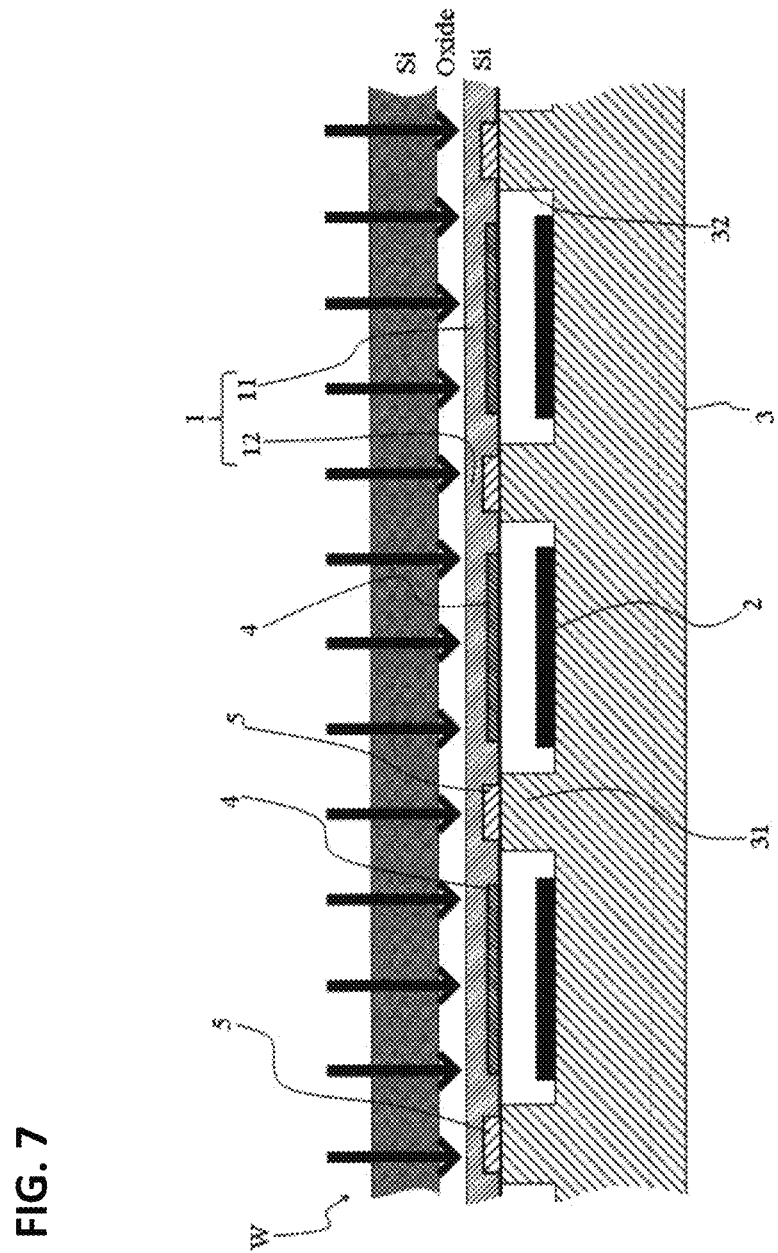
FIG. 7 is an explanation view for explaining a method for manufacturing the transducer and transducer array according to Embodiment 1 of the first present invention.

The following description will explain a method for manufacturing the transducer 10 and transducer array 100 according to Embodiment 1 of the present invention. FIGS. 5 to 7 are explanation views for explaining the method for manufacturing the transducer 10 and transducer array 100 according to Embodiment 1 of the present invention.

First, concerning an upper plate 1 side, the thermal diffusion method or ion implantation method is subjected to one side of an SOI (Silicon On Insulator) wafer W, as shown in FIG. 5(*a*) to form an impurity region to be each of the opposite electrode 4 and integrated circuit section 5, respectively (integrated-circuit-section forming process). That is, in the method for manufacturing the transducer according to Embodiment 1 of the present invention, the opposite electrode 4 and integrated circuit section 5 are simultaneously formed, thereby shortening the manufacturing process and reducing the manufacturing cost.

On the other hand, concerning a substrate 3 side, a patterning is subjected to a top face of the substrate 3 of Pyrex glass to form the recess portion 32, as shown in FIG. 5(*b*). When the patterning is subjected to the substrate 3, the holding section 31 is formed together.

Next, a vapor-deposition material (for example, Ni, Cr, Al, Pt, Au etc.) to be the substrate-side electrode 2 is subjected to a vapor-deposition. In addition, a process for vapor-depositing an insulation membrane (not shown) which insulates the substrate-side electrode 2 from the opposite electrode 4 may be performed.

Then, a top and a bottom of the SOI wafer W is inversed so that the one side of the SOI wafer W faces a top face of the substrate 3 prepared already or (the bottom of recess portion 32), and the SOI wafer W is fixed to the top face of the substrate 3, that is, the top face of the holding section 31. In detail, the one side of the SOI wafer W is bonded to the top face of the holding section 31 by the above-described anodic bonding method (see FIG. 6).

Thereafter, as shown in FIG. 7, a wet chemical etching (expressed with an arrow in the drawing) is subjected to the other side of the SOI wafer W, that is, an upper Si layer and oxide layer using TMAH, KOH, HF etc., except for a portion to be the upper plate 1, thereby the upper plate 1 is completed.

Note that it is not limited to this, and a Si wafer having a Si/Si3N4 (low stress) configuration may be used.

It is not necessary to additionally provide a so-called vibrating membrane holding section for holding the upper plate 1 (vibrating membrane section 11) in the method for manufacturing the transducer according to the present invention, as described above, thereby the number of the processes becomes low and it is not necessary to consider stress concentration, etc. in a fixed portion occurring upon fixing the vibrating membrane holding section to the substrate 3 so the manufacturing flexibility is enlarged.

Moreover, the following description will explain an action of the transducer 10 and transducer array 100 according to Embodiment 1 of the present invention. For convenience of explanation, it will explain a case where a voltage is applied to the transducer 10 and transducer array 100 and they send an ultrasonic wave to an object and receive the ultrasonic wave reflected from the object as an example.

When the transducer 10 of the transducer array 100 according to Embodiment 1 of the present invention receives the ultrasonic wave reflected from the object, the vibrating membrane section 11 vibrates by the ultrasonic wave (sound pressure). When the vibrating membrane section 11 vibrates, a gap between the vibrating membrane section 11 and the substrate-side electrode 2 of the substrate 3 varies. Therefore, a capacitance between the opposite electrode 4 formed in the bottom face of the vibrating membrane section 11 and the substrate-side electrode 2 changes. Based on the capacitance change between the opposite electrode 4 and the substrate-side electrode 2, the capacitance change is converted to a voltage change signal to obtain an electric signal, and based on the electric signal an ultrasonic image of the object can be obtained.

Also, for sending an ultrasonic wave, a DC voltage and an AC voltage are applied between the opposite electrode 4 and the substrate-side electrode 2, thereby the vibrating membrane section 11 vibrates and the ultrasonic wave is sent. The other action is performed similarly to the reception of an ultrasonic wave and the detail description thereof is omitted.

Embodiment 2

Figure 8:
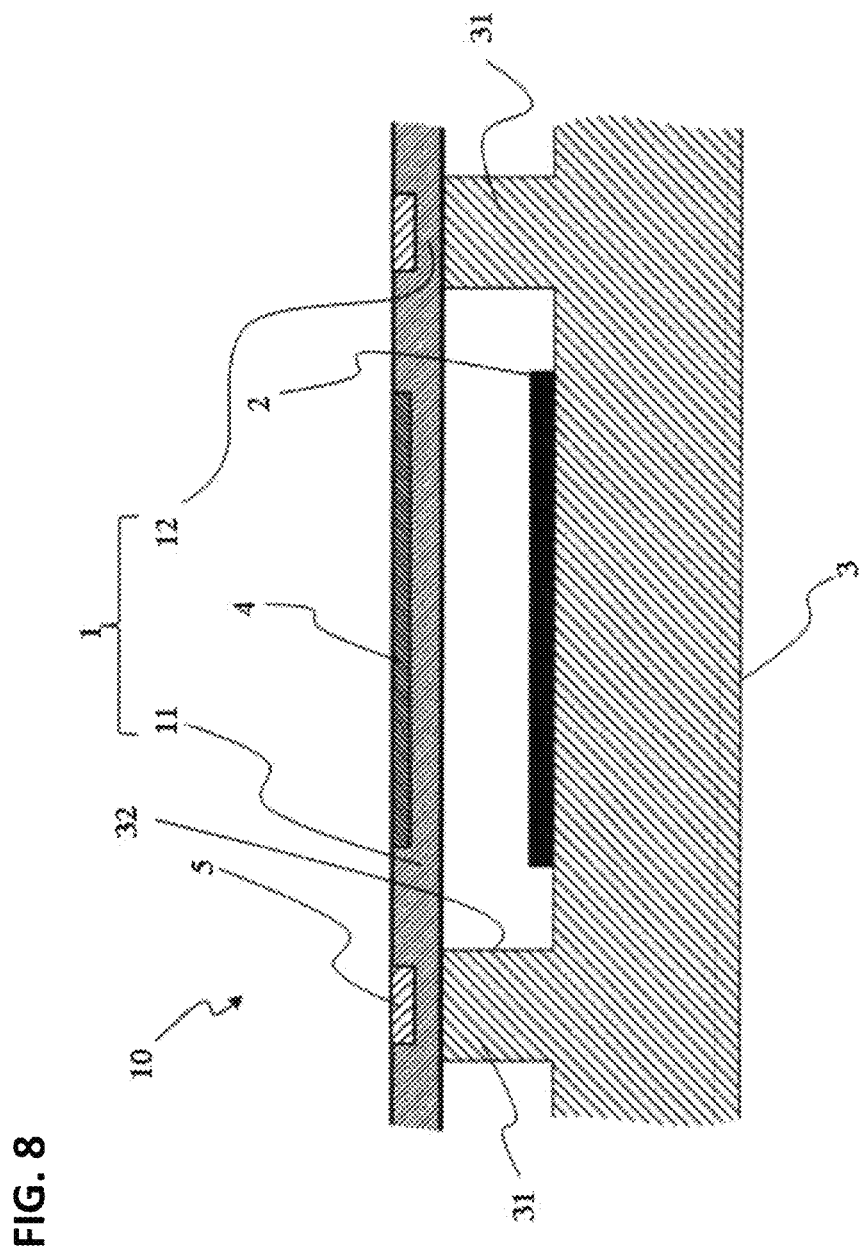
FIG. 8 is a schematic sectional view for explaining a configuration of a transducer according to Embodiment 2 of the first present invention.

FIG. 8 is a schematic sectional view for explaining a configuration of a transducer according to Embodiment 3 of the present invention.

The transducer 10 of the transducer array 100 according to Embodiment 2 of the present invention comprises the substrate 3 and the upper plate 1 arranged above the substrate 3 so as to face the substrate 3. The recess portion 32 is formed in the top face of the substrate 3 facing the bottom face of the upper plate 1, the substrate-side electrode 2 is provided in the bottom of the recess portion 32.

The upper plate 1 includes a vibrating membrane section 11 which sends or receives an ultrasonic wave, and a contact section 12 which matches to the holding section 31 and contacts the holding section 31. The bottom face of the contact section 12 is bonded to the top face of the holding section 31, and the upper plate 1 is fixed to the substrate 3.

The vibrating membrane section 11 is a part of the upper plate 1 which faces the substrate-side electrode 2. The adjacent vibrating membrane sections 11 with the contact section 12 therebetween are formed at a distance. That is, the periphery of the vibrating membrane section 11 is surrounded by the contact section 12, and the contact section 12 is bonded to the holding section 31 thereby enabling the vibration of the vibrating membrane section 11.

The upper plate 1 faces the substrate 3 and is provided to cover the recess portion 32. The thickness of the upper plate 1 is 1.5 μm, for example, but it is not limited to this and may be 0.1 to 10 μm. The upper plate 1 is made of silicon monocrystal whose resistance value is 10000 Ωcm or more, for example. Therefore, in the transducer 10 and transducer array 100 according to Embodiment 1 of the present invention, an electric charge is pooled in the vibrating membrane section 11 in applying voltage, so the charge phenomenon is preventer from occurring when the vibrating membrane section 11 is operated based on the application of AC voltage of a few to several tens of MHz.

In the top face of the vibrating membrane section 11, the opposite electrode 4 is formed. The opposite electrode 4 is an impurity region formed directly above the substrate-side electrode 2. The opposite electrode 4 is formed in a range of circle in a plan view, and is a so-called conductive impurity region obtained by subjecting an N-type or P-type chemical element to the thermal diffusion method or ion implantation method.

The integrated circuit section 5 is formed on the top face of the contact section 12. The integrated circuit section 5 is an impurity region formed at a position facing the top face of the holding section 31. In detail, the integrated circuit section 5 is an IC circuit obtained by subjecting a chemical element such as 5 group (N-type) of As, P, Sb etc. or 3 group (P-type) of Al, B, Ga etc. to the thermal diffusion method or ion implantation method at such a position of the upper plate 1.

The integrated circuit section 5 is formed to function as a variable-capacitance capacitor, a resistance, a capacitor etc. which lowers an impedance, for example. The integrated circuit section 5 is electrically connected to the opposite electrode 4, lowers an impedance occurring in the transducer 10 or transducer array 100 and has the function such as the conversion of capacitance, signal amplification and the like.

Moreover, the configuration of the transducer 10 according to Embodiment 2 of the present invention is not limited to the above description, and a configuration in which a protective membrane for protecting the opposite electrode 4 and integrated circuit section 5 is formed in the top face of the upper plate 1 may be adopted.

Moreover, in the transducer 10 according to Embodiment 2 of the present invention, the integrated circuit section 5 is formed in the contact section 12 to form an impurity region, as described above, thereby it does not require to additionally mount an element for the reduction in impedance, does not exert an influence on the vibration of the vibrating membrane section 11, and achieves the size reduction of the device, similarly to Embodiment 1.

Note that the transducer 10 according to Embodiment 2 of the present invention comprises the opposite electrode 4 formed in the upper plate 1 as the impurity region and the upper plate 1 also functions as the vibrating membrane section 11 thereby achieving the size reduction of the device further, similarly to Embodiment 1.

The other configuration is similar to that in Embodiment 1, and the same parts as in Embodiment 1 are designated with the same reference numbers, and detailed explanation thereof will be omitted.

The above description of Embodiment explains the case where the opposite electrode 4 is additionally provided in the upper plate 1, but it is not limited to this. A configuration in which the upper plate 1 also functions as the opposite electrode 4 may be adopted.

Moreover, the configuration of the transducer 10 and transducer array 100 according to the present invention is not limited to the above description. For example, the above description explains the case in which the integrated circuit section 5 is formed in the upper plate 1 only as an example, but a part of the integrated circuit section 5 may be formed in the holding section 31. That is, it may be configured so that the upper plate 1 and holding section 31 form an impurity region respectively and the impurity regions are one integrated circuit section 5 as a whole.

In a case where an impurity region is formed in the upper plate 1 or holding section 31, the impurity region may be configured not at one place but at a plurality of places of the upper plate 1 or at a plurality of places of the holding section 31.

Note that in a case where the impurity regions are formed at a plurality of places of the holding sections 31, the holding sections 31 may be configured so as to be a multilayer structure in the opposite direction of the upper plate 1 and the substrate 3, and the impurity region may be formed in each layer.

<The Mode for Implementing the Second Present Invention>

The following description will explain a transducer and a method for manufacturing the transducer according to the present invention, based on the drawings specifically. The description is made based on the example of a transducer array provided with a plurality of the transducers including two electrodes disposed opposite to each other. For convenience of explanation, the following description will explain the opposite direction of both electrodes of the transducer as a vertical direction.

Embodiment 1

FIG. 2 is a longitudinal sectional view showing a configuration of a main part of a transducer array according to Embodiment 1 of the present invention. In the drawing, the reference number 10 designates the transducer according to the present invention, and the reference number 100 designates the transducer array provided with a plurality of transducers 10. FIG. 3 is a partial schematic view showing the transducer array 100 according to Embodiment 1 of the present invention seen from above without showing a part thereof. In detail, it is a plan view in which a later-described upper plate 1 is omitted.

The following description will explain the Z axial direction as the vertical direction.

The transducer array 100 is provided with a plurality of transducers 10 disposed on one substrate 3 in the X axial direction and Y axial direction. The transducer array 100 converts an ultrasonic wave received by each transducer 10 to an electric signal, and sends it to an external device. The external device generates image data based on the electric signal sent from the transducer array 100 (transducer 10).

FIG. 4 is a schematic sectional view for explaining a configuration of the transducer 10 according to Embodiment 1 of the present invention.

The transducer 10 of the transducer array 100 according to Embodiment 1 of the present invention comprises a substrate 3 and an upper plate 1 arranged above the substrates 3 so as to face the substrate 3. A substrate-side electrode 2 is provided on a top face of the substrate 3 which faces the bottom face of the upper plate 1. A holding section 31 for holding the upper plate 1 projects towards the substrate 3 in the bottom face of the upper plate 1. In other words, the holding section 31 is arranged between the upper plate 1 and the substrate 3, a lower end part of the holding section 31 is fixed to the substrate 3, and an upper end part of the holding section 31 is fixed to the upper plate 1 through a later-described oxide layer 6. The upper plate 1, the substrate 3 and the holding section 31 form a space 32.

The upper plate 1 includes a vibrating membrane section 11 which vibrates upon sending or receiving an ultrasonic wave, and a fixed section 12 which is provided around the vibrating membrane section 11 and whose position in the vertical direction matches to the holding section 31. The fixed section 12 is fixed to the holding section 31 through the oxide layer 6.

The vibrating membrane section 11 is a part of the upper plate 1 corresponding to a position which faces the substrate-side electrode 2, and an opposite electrode 4 is formed in the vibrating membrane section 11 so as to correspond to the substrate-side electrode 2. The adjacent vibrating membrane sections 11 with the fixed section 12 therebetween are formed at a distance. That is, a periphery of the vibrating membrane section 11 is surrounded by the fixed section 12, and the fixed section 12 is fixed to the holding section 31 thereby only the vibrating membrane section 11 vibrates upon the sending or receiving.

The holding section 31 is made of silicon monocrystal, for example, and has a shape of cylinder whose top and bottom are open. The inside of the holding section 31 is a hexagon in a transversal view by a peripheral wall thereof (see FIG. 3). Also, the holding section 31 is provided so that the opposite electrode 4 is positioned at a center of the hexagon in the Z axial direction. Furthermore, the plurality of holding sections 31 have a shape of honey comb in the transducer array 100.

For example, the substrate 3 is made of glass such as Pyrex glass (registered trademark), quartz, Tempax (registered trademark), Foturanglass (registered trademark), and has a thickness of 500 μm or more, for example. As described above, the substrate-side electrode 2 is vapor-deposited on the top face of the substrate 3.

Note that the thickness of the substrate 3 is not limited to this, and may be 1 μm to 10 cm. For example, it may be 300 μm or more and 500 μm or less.

The substrate-side electrode 2 is hexagonal plate-shaped, similarly to the holding section 31, and has an area of 700 μm$^2$ or less, for example. Also, the substrate-side electrode 2 has the thickness of 0.1 to 1.0 μm, for example, and is made of a material such as Ni, Cr, Al, Pt, Au, etc. Moreover, an insulation membrane (not shown) is vapor-deposited on the top face of the substrate-side electrode 2, and the insulation membrane is made of oxide, for example and insulates the upper plate 1 (vibrating membrane section 11) from the substrate-side electrode 2.

In the holding section 31, a size of one side of the hexagon is 22 μm and a distance between opposite sides thereof is 38 μm, for example. A shape of the inside of the holding section 31 is not limited to a hexagon in a transversal view, but may be circle.

A height (size in the vertical direction) of the holding section 31, in other words, a gap between the bottom face of the upper plate 1 and the top face of the substrate 3 is 0.05 to 10 μm, for example. It is more preferred that it is 0.1 to 3 μm. Also, the holding section 31 has a wall thickness (a size in the lateral direction) of 8 to 16 μm, for example. Note that the lower end face of the holding section 31 is bonded to the top face of substrate 3 by the anodic bonding method, for example.

Accordingly, the transducer 10 according to Embodiment 1 of the present invention controls stress concentration due to the deformation which tends to occur in the process of bonding at a high temperature, and the stress concentration occurring in a bond portion between the holding section 31 and the upper plate 1. Furthermore, it controls the lowering of the conversion efficiency or sensitivity due to the stress's influence on the vibrating membrane section 11, and has an excellent structural reproducibility in manufacturing.

The case in which the wall thickness of the holding section 31 is 8 to 16 μm is explained as an example in the present Embodiment, but it is not limited to this. For example, the wall thickness may be 1 to 16 μm.

The upper plate 1 faces the substrate 3 and is provided so as to cover the holding section 31. Therefore, the upper plate 1, the substrate 3 and the holding section 31 form the space 32, as described above.

The thickness of the upper plate 1 is 1.5 μm, for example, but it is not limited to this and may be 0.1 to 10 μm.

In the bottom face of the vibrating membrane section 11, an opposite electrode 4 corresponding to the substrate-side electrode 2 is formed. The opposite electrode 4 is an impurity region formed directly above the substrate-side electrode 2. The opposite electrode 4 is formed in a range of circle in a plan view, and is a so-called conductive impurity region obtained by subjecting an N-type or P-type chemical element to a thermal diffusion method or an ion implantation method, for example.

An integrated circuit section 5 is formed on a lower end part of the holding section 31. The integrated circuit section 5 is a conductive impurity region for performing a processing concerning an electrical signal generated by a capacitance change between the substrate-side electrode 2 and the opposite electrode 4. In detail, the integrated circuit section 5 is an IC circuit obtained by subjecting a chemical element such as 5 group (N-type) of As, P, Sb etc. or 3 group (P-type) of Al, B, Ga etc. to the thermal diffusion method or ion implantation method at such a position of the holding section 31. Note that the position at which the integrated circuit section 5 is formed is not limited to this, and the integrated circuit section 5 may be formed at every places of the holding section 31.

The integrated circuit section 5 is formed to function as a variable-capacitance capacitor, a resistance, a capacitor etc. which lowers an impedance, for example. The integrated circuit section 5 is electrically connected to the opposite electrode 4, lowers an impedance occurring in the transducer 10 or transducer array 100, and has the function such as the conversion of capacitance, signal amplification, signal amplification and the like.

The transducer 10 according to Embodiment 1 of the present invention comprises the integrated circuit section 5 as described above, therefore, it can avoid the problem of impedance increase at a high frequency or in a case where the number of the transducers is low, and the problem in which a so-called parasitic capacitance occurs so an efficient lowers in a case where silicon monocrystal is used as the vibrating membrane, before something happens.

Moreover, in the transducer 10 according to Embodiment 1 of the present invention, the integrated circuit section 5 is an impurity region formed in the lower end part of the holding section 31 as described above, thereby it does not require to additionally mount a peripheral circuit for the reduction in impedance and signal processing, does not exert an influence on the vibration of the vibrating membrane section 11, and achieves the size reduction of the transducer itself and device.

Moreover, the transducer 10 according to Embodiment 1 of the present invention comprises the opposite electrode 4 and integrated circuit section 5 formed in the bottom face of the upper plate 1 and the lower end part of the holding section 31 respectively, so it does not require a protective membrane for protecting the opposite electrode 4 and integrated circuit section 5.

Note that the transducer 10 according to Embodiment 1 of the present invention comprises the opposite electrode 4 formed in the upper plate 1 as the impurity region and a part of the upper plate 1 (vibrating membrane section 11) also functions as the so-called vibrating membrane thereby achieving the size reduction of the device further.

The transducer array 100 according to Embodiment 1 of the present invention applies voltage between the substrate-side electrode 2 and the opposite electrode 4 of the upper plate 1 corresponding to the substrate-side electrode 2 in each of the plurality of transducers 10, thereby vibrating the vibrating membrane section 11 to send an ultrasonic wave to the outside, and obtaining an electric signal concerning a change of a capacitance between the substrate-side electrode 2 and the opposite electrode 4 due to the vibration of the vibrating membrane section 11 based on the ultrasonic wave reflected from the outside to obtain a so-called ultrasonic image based on the electric signal.

The following description will explain a method for manufacturing the transducer 10 and transducer array 100 according to Embodiment 1 of the present invention. FIGS. 5 and 6 are explanation views for explaining the method for manufacturing the transducer 10 and transducer array 100 according to Embodiment 1 of the present invention.

First, concerning an upper plate 1 side, the thermal diffusion method or ion implantation method is subjected to one side of an SOI (Silicon On Insulator) wafer W, as shown in FIG. 5(a) to form an impurity region to be the opposite electrode 4.

Subsequently, an oxide layer is formed in the one side of the SOI wafer W. For example, the SOI wafer W is subjected to an oxidative atmosphere in a furnace under high temperature to form the oxide layer in the one side of the SOI wafer W. By such a process, the oxide layer to be the oxide layer 6 is formed.

Next, a wafer of silicon monocrystal, for example is bonded on the formed oxide layer to form a silicon layer having an appropriate thickness. By such a process, a silicon monocrystal layer to be the holding section 31 is formed.

Next, a chemical element such as 5 group (N-type) of As, P, Sb etc. or 3 group (P-type) of Al, B, Ga etc. is subjected on the formed silicon layer to the thermal diffusion method or ion implantation method to form an impurity region (integrated-circuit-section forming process). The impurity region corresponds to the above-described integrated circuit section 5.

On the other hand, concerning a substrate 3, a vapor-deposition material (for example, Ni, Cr, Al, Pt, Au etc.) to be the substrate-side electrode 2 is subjected to vapor-deposition on a top face of the substrate 3 of Pyrex glass, as shown in FIG. 5(b). In addition, a process for vapor-depositing an insulation membrane (not shown) which insulates the substrate-side electrode 2 from the opposite electrode 4 may be performed.

As described above, after the impurity region is formed, as shown in FIG. 6(a), a patterning and etching are performed on a face of the silicon layer. For example, wet chemical etching (expressed with an arrow in the drawing) is performed using TMAH, KOH, HF etc., to remove the silicon layer and oxide layer except for a portion to be the holding section 31 and the oxide layer 6. The patterning may be performed by the dry etching method. The holding section 31 and oxide layer 6 are completed by such a process.

Then, a top and a bottom of the SOI wafer W is inversed so that the one side of the SOI wafer W faces a top face of the substrate 3 prepared already, and the SOI wafer W is fixed to the top face of the substrate 3 via the holding section 31. In detail, the lower end face of peripheral wall of the holding section 31 is bonded to the top face of the holding section 31 by the above-described anodic bonding method.

Thereafter, as shown in FIG. 6(b), a wet chemical etching (expressed with an arrow in the drawing) is subjected to the other side of the SOI wafer W, that is, an upper Si layer and oxide layer using TMAH, KOH, HF etc., except for a portion to be the upper plate 1, thereby the upper plate 1 is completed.

Note that it is not limited to this, and a Si wafer having a Si/Si3N4 (low stress) configuration may be used instead of the SOI wafer.

Moreover, the following description will explain an action of the transducer 10 and transducer array 100 according to Embodiment 1 of the present invention. For convenience of explanation, it will explain a case where a voltage is applied to the transducer 10 and transducer array 100 and they send an ultrasonic wave to an object and receive the ultrasonic wave reflected from the object as an example.

When the transducer 10 of the transducer array 100 according to Embodiment 1 of the present invention receives the ultrasonic wave reflected from the object, the vibrating membrane section 11 vibrates by the ultrasonic wave (sound pressure). When the vibrating membrane section 11 vibrates, a gap between the vibrating membrane section 11 and the substrate-side electrode 2 of the substrate 3 varies. Therefore, a capacitance between the opposite electrode 4 formed in the bottom face of the vibrating membrane section 11 and the substrate-side electrode 2 changes. Based on the capacitance change between the opposite electrode 4 and the substrate-side electrode 2, the capacitance change is converted to a voltage change signal to obtain an electric signal, and based on the obtained electric signal an ultrasonic image of the object can be obtained.

Also, for sending an ultrasonic wave, a DC voltage and an AC voltage are applied between the opposite electrode 4 and the substrate-side electrode 2, thereby the vibrating membrane section 11 vibrates and the ultrasonic wave is sent. The other action is performed similarly to the reception of an ultrasonic wave and the detail description thereof is omitted.

Embodiment 2

The configuration of the transducer 10 of the transducer array 100 according to Embodiment 2 of the present invention is substantially similar to that in Embodiment 1, but the configuration of the integrated circuit section 5 formed in the holding section 31 is different from that in Embodiment 1.

FIG. 7 is a schematic sectional view for explaining a configuration of the transducer 10 according to Embodiment 2 of the second present invention.

The transducer 10 of the transducer array 100 according to Embodiment 2 of the present invention comprises two integrated circuit sections 5, 5 formed in the lower end part of the holding section 31. In detail, a trench 61 is provided in the holding section 31, thereby the holding section 31 is divided into a plurality of regions to form the respective integrated circuit section 5. Each integrated circuit section 5 is an impurity region for performing a processing concerning an electrical signal generated by a capacitance change between the substrate-side electrode 2 and the opposite electrode 4. Note that the trench 61 may be omitted, and a plurality of trenches 61 may be provided.

Next, as a method for forming the two integrated circuit sections 5, a chemical element such as 5 group (N-type) of As, P, Sb etc. or 3 group (P-type) of Al, B, Ga etc. is subjected at two places of the silicon layer to the thermal diffusion method or ion implantation method in the above-described integrated-circuit-section forming process.

The integrated circuit section 5 is formed to function as a variable-capacitance capacitor, a resistance, a capacitor etc. which lowers an impedance. The integrated circuit section 5 is electrically connected to the opposite electrode 4, lowers an impedance occurring in the transducer 10 or transducer array 100 and has the function such as the conversion of capacitance, signal amplification and the like. The function may be performed by the two integrated circuit section 5, 5, respectively, or may be shared by them appropriately.

The above description explains a case where the two integrated circuit sections 5, 5 are formed in the lower end part of the holding section 31, but it is not limited to this. Two or more of the integrated circuit sections may be formed. That is, the integrated circuit section 5 can be provided also in the upper part of the holding section 31. In addition, the integrated circuit section 5 may be configured so that the trench 61 etc. is provided, the holding section 31 is divided to a plurality of regions and a plurality of the integrated circuit sections 5 having various functions are formed there.

Embodiment 3

The configuration of the transducer 10 of the transducer array 100 according to Embodiment 3 of the present invention is substantially similar to that in Embodiment 1, but the configurations of the holding section 31 and the integrated circuit section 5 formed in the holding section 31 are different from that in Embodiment 1.

FIG. 8 is a schematic sectional view for explaining a configuration of a transducer 10 according to Embodiment 3 of the present invention.

In the transducer 10 of transducer array 100 according to Embodiment 3 of the present invention, the holding section 31 has a multilayer structure provide with a plurality of silicon layers. An oxide layer 6 is disposed between the silicon layers.

The integrated circuit section 5 is formed in each silicon layer of the holding section 31. In other words, the integrated circuit section 5 is formed above each oxide layer 6 of the holding section 31. The integrated circuit section 5 is an impurity region for performing a processing concerning an electrical signal generated by a capacitance change between the substrate-side electrode 2 and the opposite electrode 4.

Figure 9:
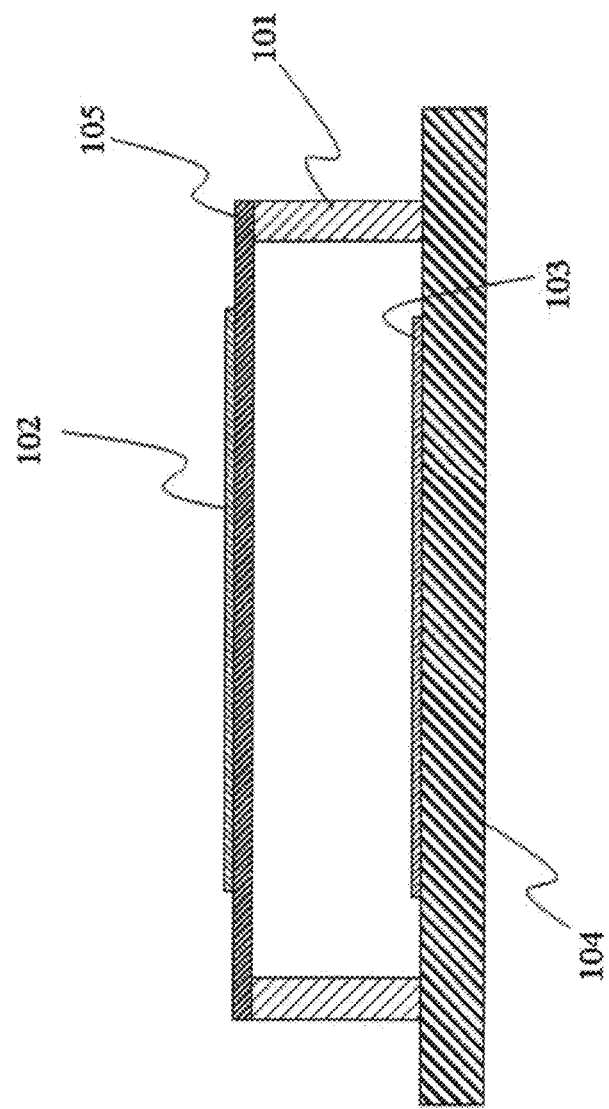
FIG. 9 is an explanation view for explaining a method for manufacturing the transducer and transducer array according to Embodiment 3 of the second present invention.

The following description will explain a method for forming the holding section 31 and the integrated circuit section 5 in the transducer 10 or transducer array 100 according to Embodiment 3 of the present invention. FIG. 9 is an explanation view for explaining a method for manufacturing the transducer 10 and transducer array 100 according to Embodiment 3 of the second present invention.

First, concerning an upper plate 1 side, the thermal diffusion method or ion implantation method is subjected to one side of an SOI wafer W, as shown in FIG. 5(*a*) to form an impurity region to be the opposite electrode 4. Thereafter, an oxide layer to be the oxide layer 6 is formed in the one side of the SOI wafer W.

Next, a wafer of silicon monocrystal, for example is bonded on the formed oxide layer, and the thickness of the wafer is adjusted with a method such as etching to form a layer 1 of a silicon layer. By such a process, the silicon layer to be a part of the holding section 31 is formed.

Next, an impurity region corresponding to the integrated circuit section 5 is formed in the formed layer 1 of silicon layer by the thermal diffusion method or ion implantation method, as described above (integrated-circuit-section forming process).

Then, an oxide layer is formed on the layer 1 of silicon layer, again. Subsequently, a layer 2 of a silicon layer is formed on the formed oxide layer. In addition, an impurity region corresponding to the other integrated circuit section 5 is formed in the formed layer 2 of the silicon layer.

By repeating such a process, a predetermined number of the silicon layers and corresponding integrated circuit sections 5 are formed. Then, as shown in FIG. 6(*a*), the patterning and etching are performed. The subsequent process is explained already, and the detail description thereof is omitted.

The integrated circuit section 5 is formed to function as a variable-capacitance capacitor, a resistance, a capacitor etc. which lowers an impedance, for example. The integrated circuit section 5 is electrically connected to the opposite electrode 4, lowers an impedance occurring in the transducer 10 or transducer array 100 and has the function such as the conversion of capacitance, signal amplification and the like. The function may be performed by the two integrated circuit section 5, 5, respectively, or may be shared by them appropriately.

In the transducer 10 of transducer array 100 according to Embodiment 3 of the present invention, it is possible to efficiently form a plurality of the integrated circuit sections 5 in the holding section 31, as described above, thereby achieving the size reduction of the transducer itself and the device in which the transducer is mounted. Each integrated circuit section 5 is blocked by the oxide layer 6, thereby preventing the mutual interference before something happens.

Embodiment 4

The configuration of the transducer 10 of the transducer array 100 according to Embodiment 4 of the present invention is substantially similar to that in Embodiment 3, but the configurations of the substrate 3 is different from that in Embodiment 3.

Figure 10:
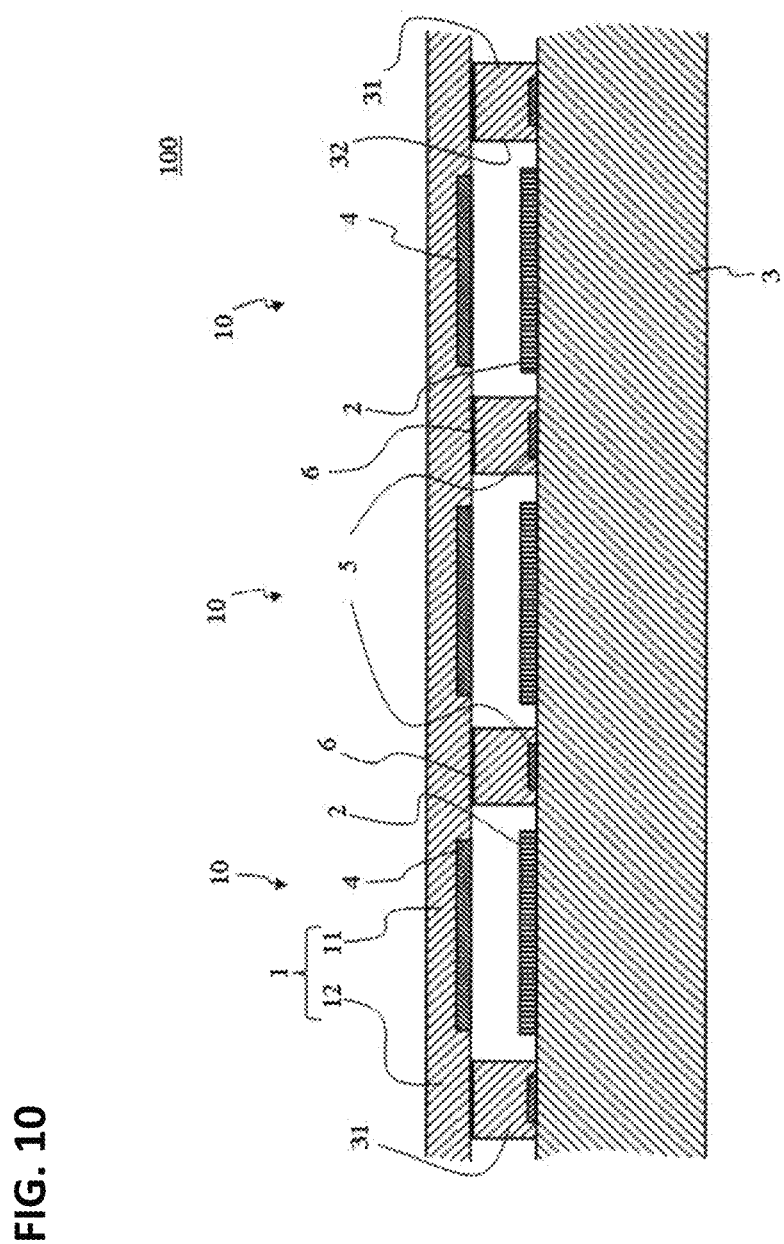
FIG. 10 is a schematic sectional view for explaining a configuration of a transducer according to Embodiment 4 of the second present invention.
Figure 11:
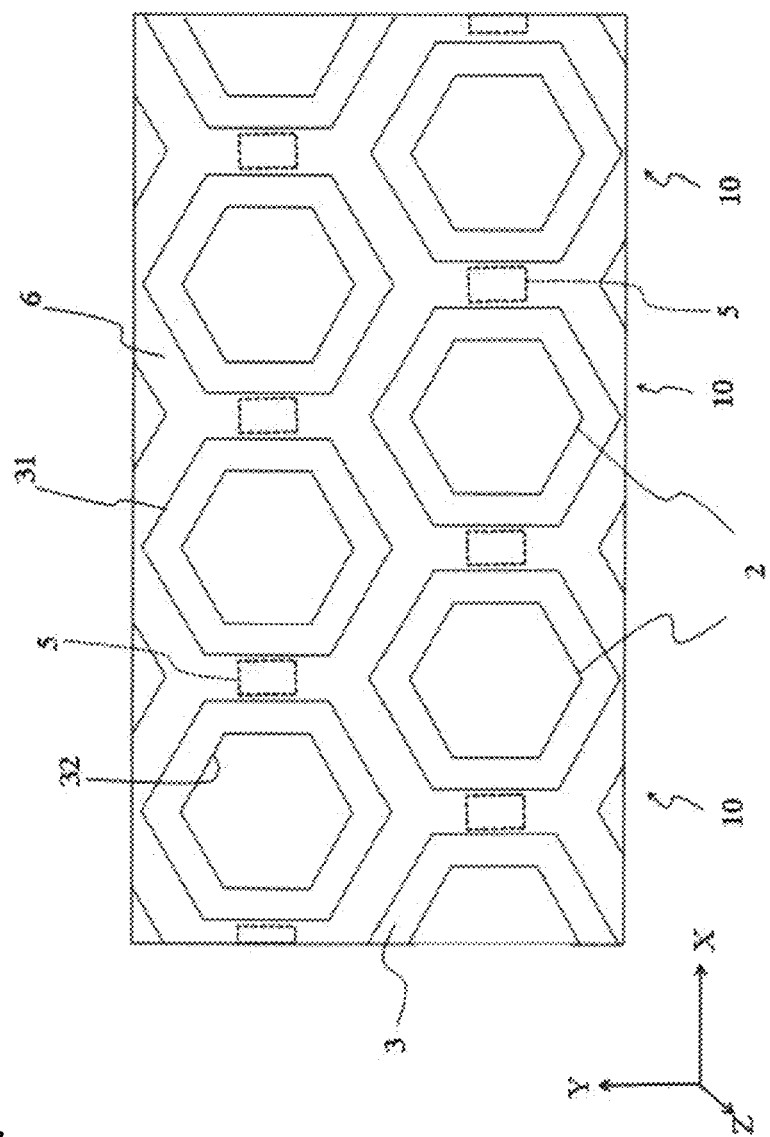
Figure 12:
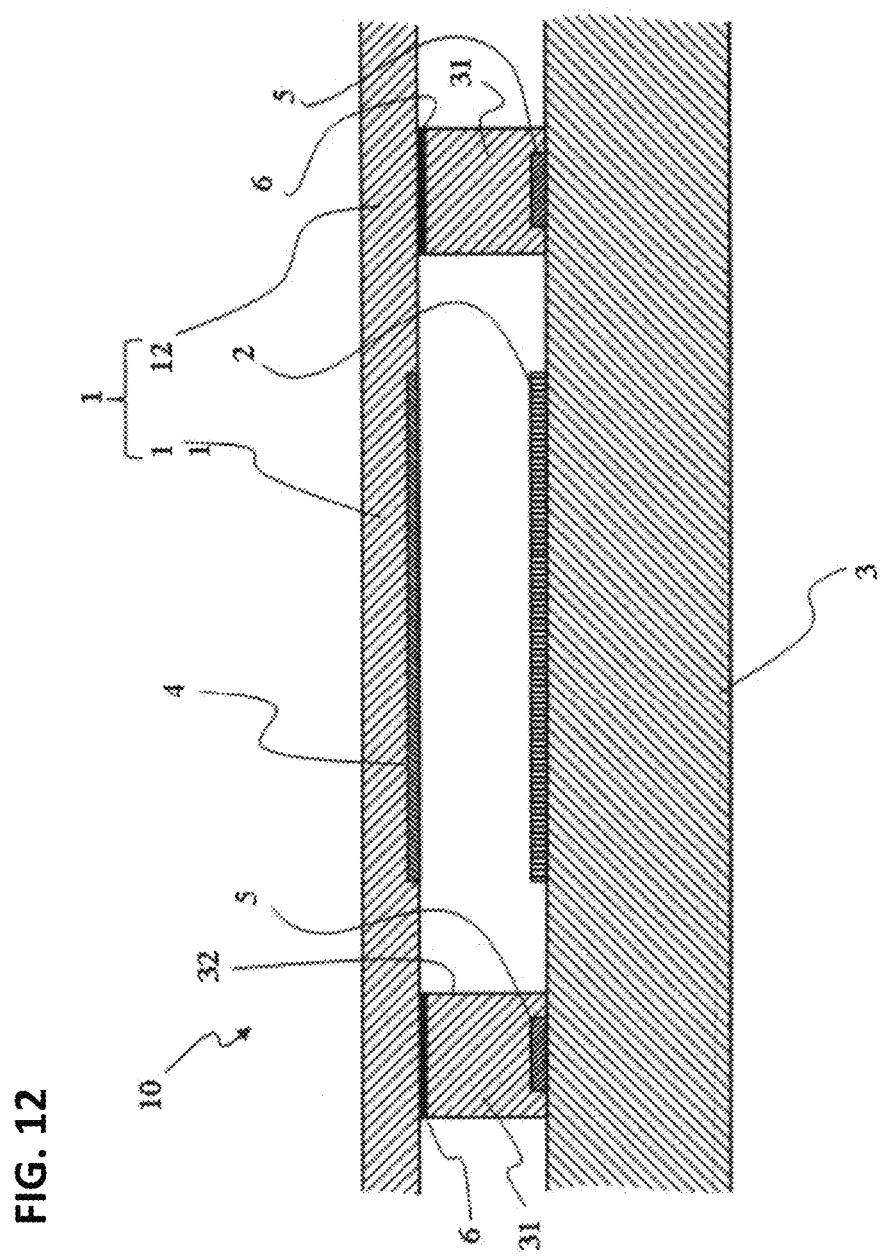
Figure 13:
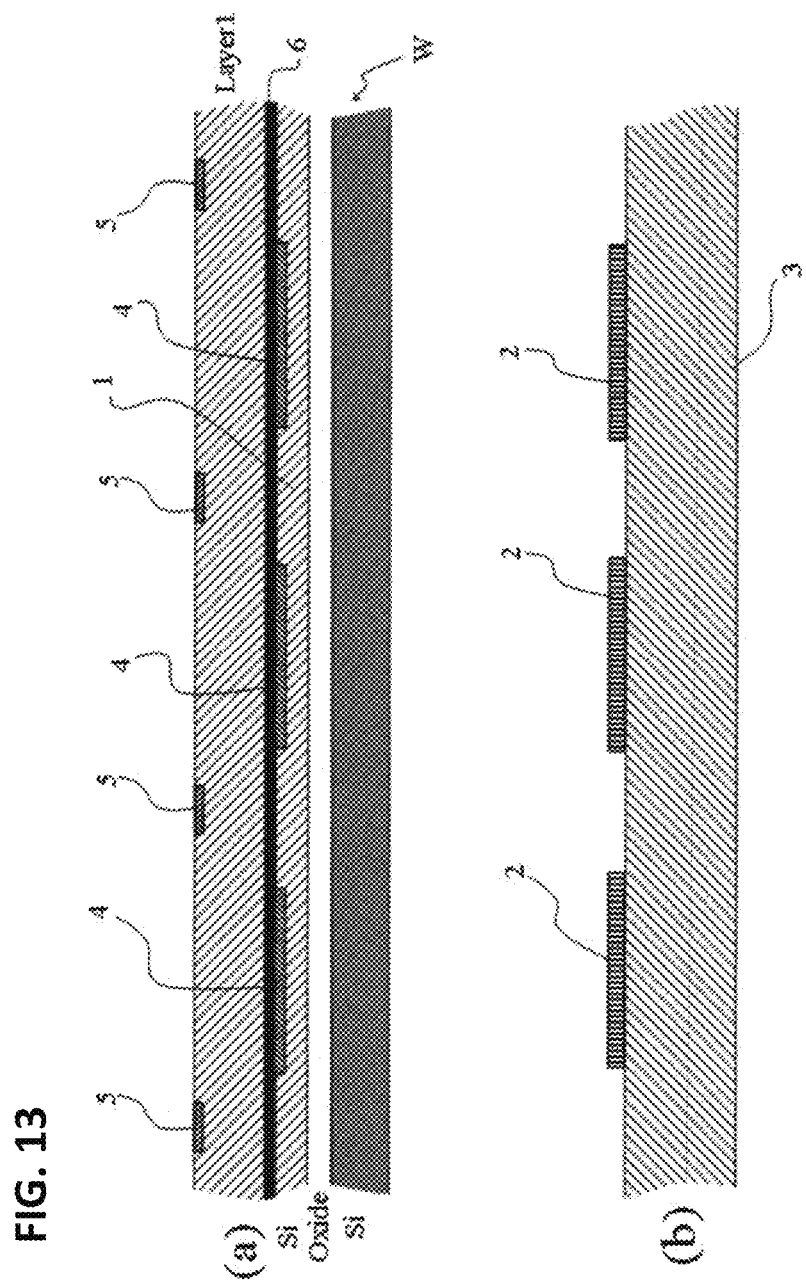
Figure 14:
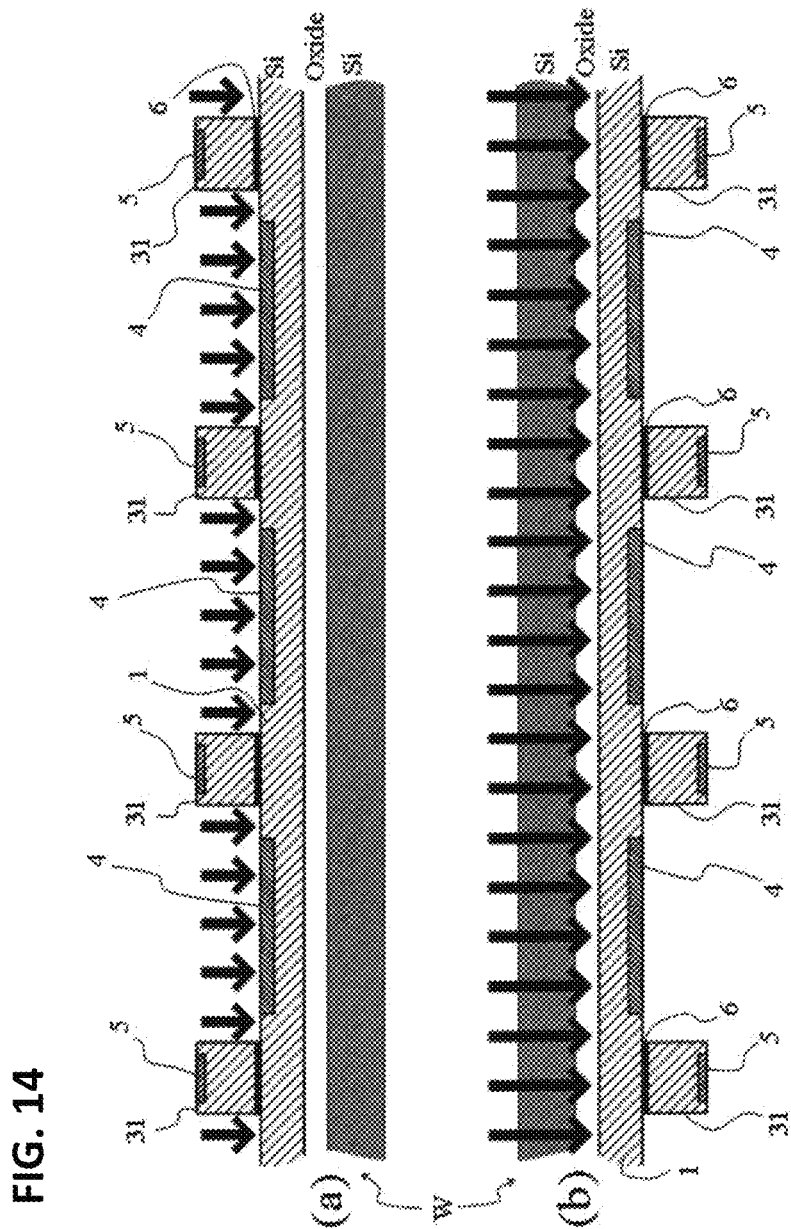
Figure 15:
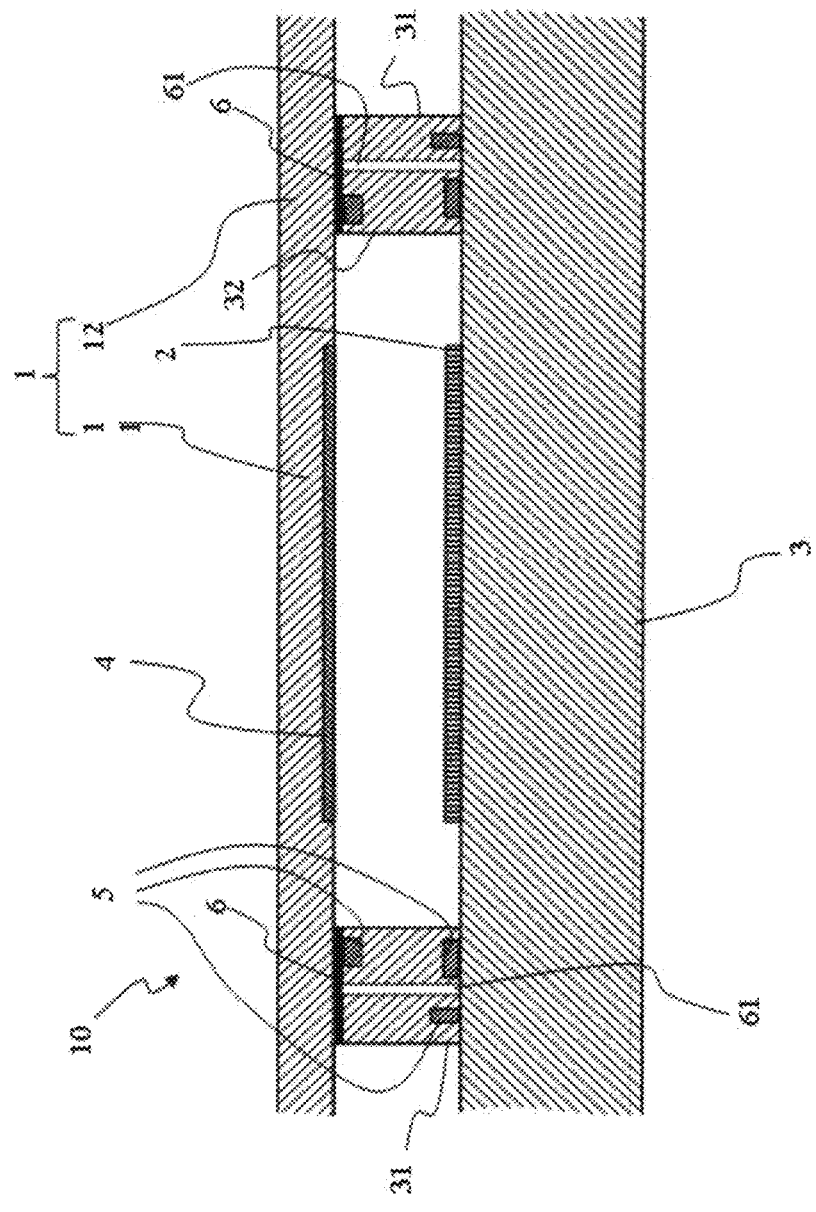
Figure 16:
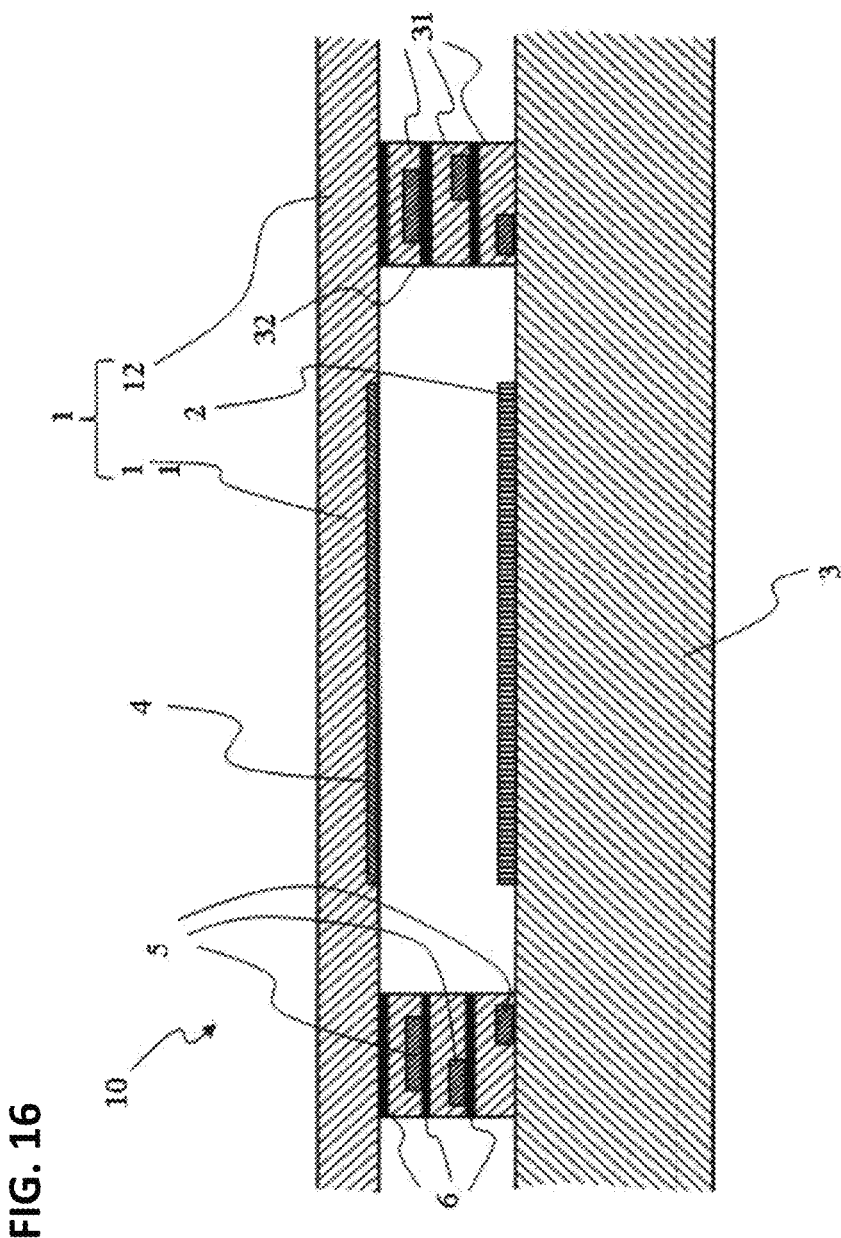
Figure 17:
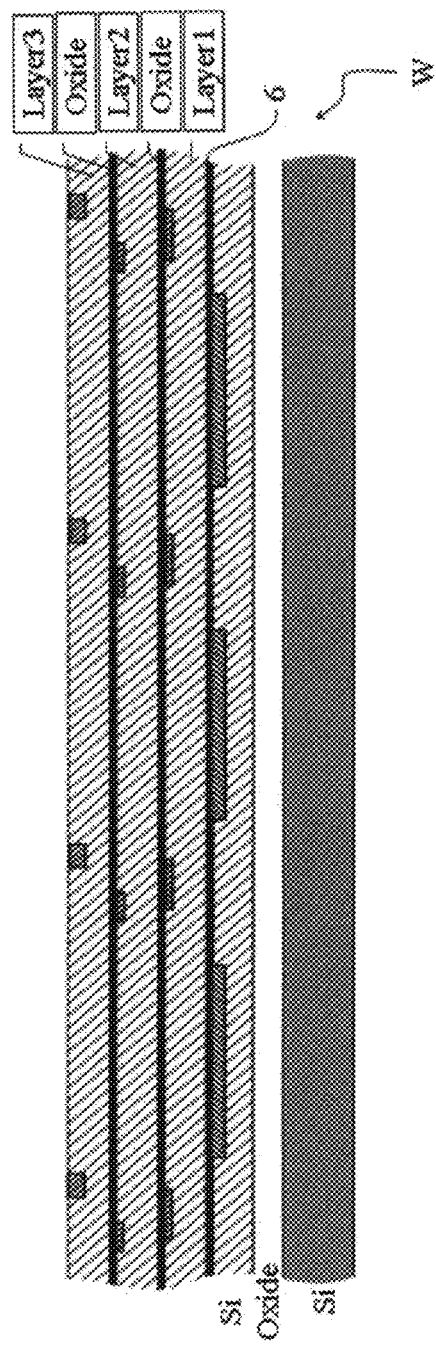
Figure 18:
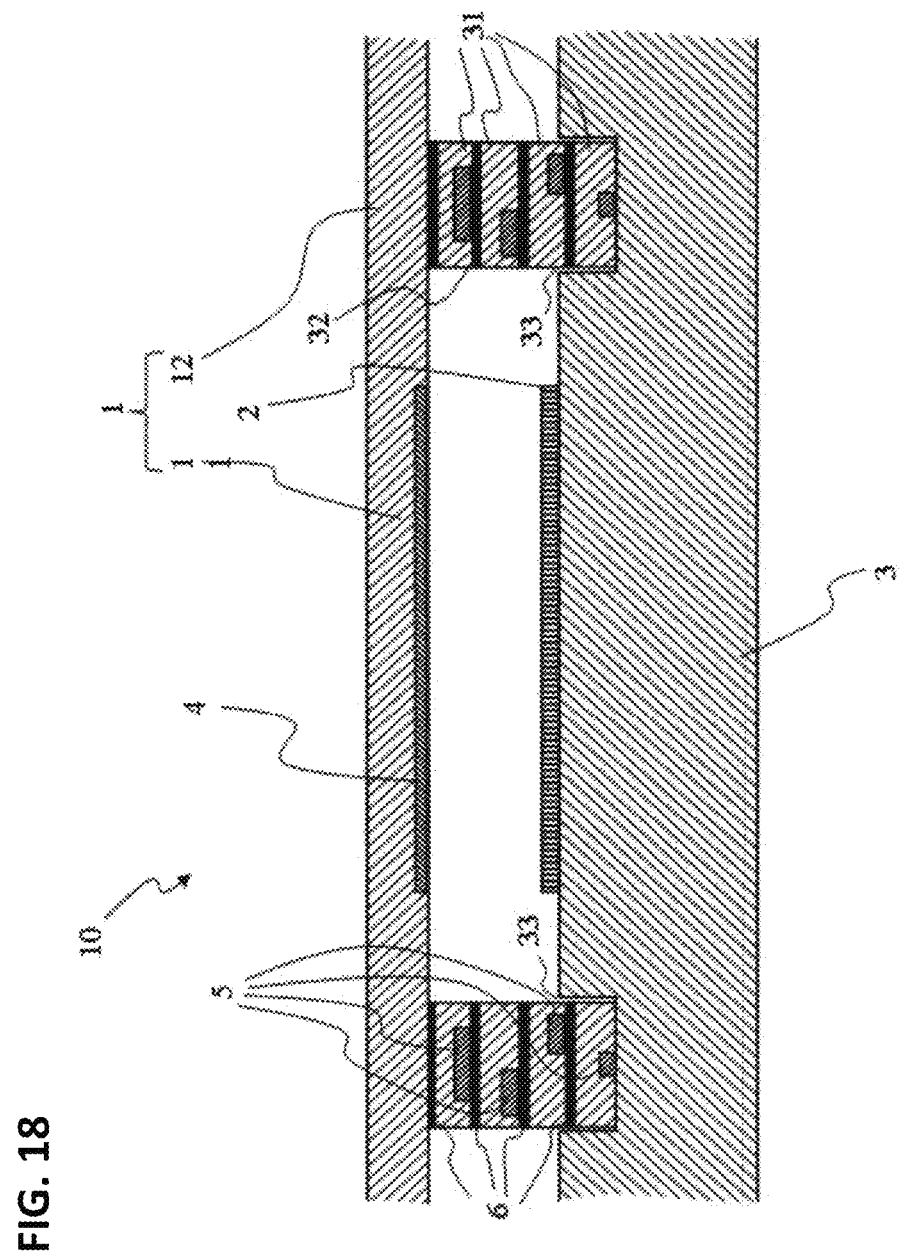

FIG. 10 is a schematic sectional view for explaining a configuration of a transducer 10 according to Embodiment 4 of the second present invention.

In the transducer 10 of transducer array 100 according to Embodiment 4 of the present invention, the holding section 31 has a multilayer structure provided with a plurality of silicon layers, similarly to Embodiment 3. An oxide layer 6 is disposed between the silicon layers. The integrated circuit section 5 is formed in each silicon layer.

On the other hand, a groove section 33 is formed in the top face of the substrate 3 along a lower end portion of a peripheral wall of the holding section 31. The inside of the groove section 33 is U-shaped in a vertical view, similarly to the shape of the lower end portion of the peripheral wall of the holding section 31, and the groove section 33 has a hexagonal shape in a plan view.

A gap between the opposite side faces of the groove section 33 is larger than the size of a wall thickness of the holding section 31. Therefore, a lower end part of the holding section 31 (peripheral wall) can be inserted into the groove section 33.

That is, in the process of manufacturing the transducer array 100 (transducer 10) according to Embodiment 4 of the present invention, when the lower end portion of the peripheral wall of the holding section 31 is bonded to the substrate 3 by the anodic bonding method, the lower end portion of the peripheral wall of the holding section 31 is bonded to the bottom of the groove section 33 in a condition where it is inserted into the groove section 33. This allows a gap between the upper plate 1 (opposite electrode 4) and the substrate 3 (substrate-side electrode 2) to be adjusted by changing the depth (size in the Z axial direction) of the groove section 33 from the height of the holding section 31.

In other words, the depth of the groove section 33 is a predetermined value according to the height of the holding section 31. For example, in a case where the height of the holding section 31 is larger than a gap between the substrate-side electrode 2 and the opposite electrode 4, the depth of the groove section 33 is determined so as to keep the gap constant.

Accordingly, the height or the number of the layer of the holding section 31 is increased to form a plurality of the integrated circuit sections 5 in the holding section 31 having the multilayer structure in the transducer 10 of transducer array 100 according to Embodiment 4 of the present invention. Therefore, the gap between the substrate-side electrode 2 and the opposite electrode 4 can be kept constant by appropriately adjusting the depth of the groove section 33 even when the height of the holding section 31 is large. That is, such a configuration can be applied even in a case where the height of the holding section 31 is increased because the holding section 31 has the multilayer structure or has a single-layer structure whose thickness is large.

Moreover, the configuration of the transducer 10 and transducer array 10 according to the present invention is not limited to the above description. For example, the above description explains the case where the integrated circuit section 5 is formed in the holding section 31 only, but a part of the integrated circuit section 5 may be formed in the upper plate 1. That is, the holding section 31 and the upper plate 1 form an impurity region, respectively.

What is claimed is:

1. A transducer comprising a substrate-side electrode provided in one side of an insulative substrate and an opposite plate including an opposite electrode disposed opposite to the substrate-side electrode, the transducer generating a signal based on a change of a gap between the substrate-side electrode and the opposite electrode, wherein the opposite plate is made of silicon monocrystal, and is provided with an integrated circuit section for performing a processing concerning the signal.

2. The transducer according to claim 1, wherein the integrated circuit section is an impurity region, and is electrically connected to the opposite electrode.

3. The transducer according to claim 1, further comprising a holding section which is provided in the substrate so as to project and holds the opposite plate,
wherein the integrated circuit section is provided at a position which matches the holding section.

4. The transducer according to claim 1, wherein the opposite plate is provided in one side of the opposite plate facing the substrate and at a position where the opposite plate contacts the holding section.

5. A method for manufacturing a transducer comprising a substrate-side electrode provided in one side of an insulative substrate and an opposite plate including an opposite electrode disposed opposite to the substrate-side electrode, the transducer generating a signal based on a change of a gap between the substrate-side electrode and the opposite electrode, comprising
an integrated-circuit-section forming process of forming an integrated circuit section for performing a processing concerning the signal in an opposite plate made of silicon monocrystal.

6. The method for manufacturing a transducer according to claim 5, wherein the integrated circuit section is an impurity region, and is electrically connected to the opposite electrode.

7. The method for manufacturing a transducer according to claim 5, wherein in the integrated-circuit-section forming process, the opposite electrode is formed.

8. A transducer comprising a substrate-side electrode provided in one side of an insulative substrate and an opposite plate including in one side an opposite electrode disposed opposite to the substrate-side electrode, the transducer generating a signal based on a change of a gap between the substrate-side electrode and the opposite electrode, further comprising:
a holding section which is provided in one side of the opposite plate so as to project and holds the opposite plate; and
an integrated circuit section which is provided in the holding section and performs a processing concerning the signal.

9. The transducer according to claim 8, wherein the integrated circuit section is an impurity region, and is electrically connected to the opposite electrode.

10. The transducer according to claim 8, wherein the holding section is provided with the integrated circuit sections at a plurality of places.

11. The transducer according to claim 8, wherein the holding section includes a multilayer structure, and
the integrated circuit sections are provided in a plurality of layers.

12. The transducer according to claim 8, wherein a groove section is provided in the one side of the substrate, and
an end part of the holding section on a side of the substrate is inserted into the groove section.

13. The transducer according to claim 12, wherein the groove section is configured so that sizes in an opposite direction of the substrate-side electrode and the opposite electrode are sizes according to a size of the holding section in the opposite direction.

14. A method for manufacturing a transducer comprising a substrate-side electrode provided in one side of an insulative substrate and an opposite plate including in one side an opposite electrode disposed opposite to the substrate-side electrode, the transducer generating a signal based on a change of a gap between the substrate-side electrode and the opposite electrode, comprising an integrated-circuit-section forming process of forming an integrated circuit section for performing a processing concerning the signal in a holding section which is provided in one side of the opposite plate so as to project and holds the opposite plate.

15. The method for manufacturing a transducer according to claim 14, wherein the integrated circuit section is an impurity region, and is electrically connected to the opposite electrode.

16. The method for manufacturing a transducer according to claim 14, wherein the holding section is formed by a lamination process, and during the lamination process the integrated-circuit-section forming process is performed.

* * * * *